United States Patent

Sato et al.

[11] Patent Number: 5,202,335
[45] Date of Patent: Apr. 13, 1993

[54] SUCCINIC ACID COMPOUNDS

[75] Inventors: Fumiyasu Sato; Atsushi Tsubaki; Hiroshi Hokari; Nobuyuki Tanaka; Masaru Saito; Kenji Akahane; Michihiro Kobayashi, all of Nagano, Japan

[73] Assignee: Kissei Pharmaceutical Co., Ltd., Nagano, Japan

[21] Appl. No.: 860,023

[22] Filed: Mar. 30, 1992

[30] Foreign Application Priority Data

Mar. 30, 1991 [JP] Japan ................. 3-142275
Apr. 25, 1991 [JP] Japan ................. 3-188416
Dec. 27, 1991 [JP] Japan ................. 3-361519

[51] Int. Cl.$^5$ .................. A61K 31/47; A61K 31/40; C07D 209/44; C07D 217/06
[52] U.S. Cl. .................. 514/307; 514/412; 546/147; 548/452; 548/515
[58] Field of Search .............. 548/515, 452; 546/147; 514/412, 307

[56] References Cited

U.S. PATENT DOCUMENTS 4,303,662 12/1981 Sprague ................. 514/412 X

FOREIGN PATENT DOCUMENTS 8303828 11/1983 World Int. Prop. O. .......... 548/452

Primary Examiner—Mary C. Lee
Assistant Examiner—Michael G. Ambrose
Attorney, Agent, or Firm—Sughrue, Mion, Zinn, Macpeak & Seas

[57] ABSTRACT

Succinic acid compounds of the formula:

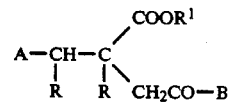

wherein A represents a heterocyclic group, a 3 to 8-membered cycloalkyl group or a phenyl group which may have one or more substituents selected from the group of a halogen atom, a lower alkyl group having 1 to 6 carbon atoms and a lower alkoxy group having 1 to 6 carbon atoms; B represents a bicyclic amino group which may have 1 or 2 unsaturated bonds, with the proviso that B bonds to the carbon atom of the carbonyl group at the nitrogen atom; R represents a hydrogen atom or combines each other to form a chemical bond; $R^1$ represents a hydrogen atom, a lower alkyl group having 1 to 6 carbon atoms or an aralkyl group having 7 to 10 carbon atoms; when there is an asymmetric carbon atom, enantiomers thereof and racemic mixtures thereof; when there are geometrical isomers, each geometrical isomer, E-isomers thereof, Z-isomers thereof, cis-isomers thereof and trans-isomers thereof; and pharmaceutically acceptable salts thereof, enhance insulin secretion and possess a hypoglycemic activity, and are thus useful for the treatment of diabetes.

9 Claims, No Drawings

SUCCINIC ACID COMPOUNDS

FIELD OF THE INVENTION

The present invention relates to succinic acid compounds being useful as a therapeutic agent for the treatment of diabetes.

More particularly, the present invention relates to novel succinic acid compounds represented by the formula:

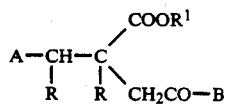

wherein A represents a heterocyclic group, a 3 to 8-membered cycloalkyl group or a phenyl group which may have one or more substituents selected from the group of a halogen atom, a lower alkyl group having 1 to 6 carbon atoms and a lower alkoxy group having 1 to 6 carbon atoms; B represents a bicyclic amino group which may have 1 or 2 unsaturated bonds, with the proviso that B bonds to the carbon atom of the carbonyl group at the nitrogen atom; R represents a hydrogen atom or combines each other to form a chemical bond; $R^1$ represents a hydrogen atom, a lower alkyl group having 1 to 6 carbon atoms or an aralkyl group having 7 to 10 carbon atoms; when there is an asymmetric carbon atom, enantiomers thereof and racemic mixtures thereof; when there are geometrical isomers, each geometrical isomer, E-isomers thereof, Z-isomers thereof, cis-isomers thereof and trans-isomers thereof; and pharmaceutically acceptable salts thereof.

Narrower classes of compounds within formula (I) include those represented by the formulae:

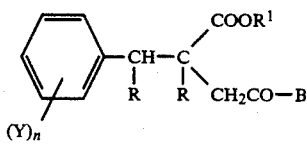

wherein Y represents a halogen atom, a lower alkyl group having 1 to 6 carbon atoms, or a lower alkoxy group having 1 to 6 carbon atoms, n represents 0, 1, or 2 and other groups are as defined for formula (I);

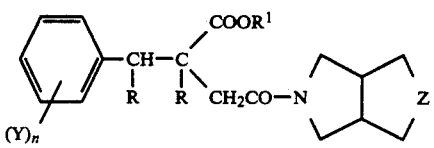

wherein Y and n are as above defined and Z presents an ethylene group or a vinylene group;

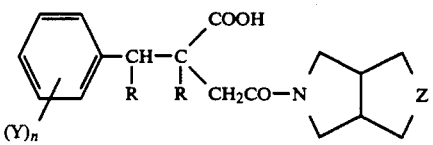

wherein Y and n are as above defined and Z represents and ethylene group or a vinylene group and other groups are as defined for formula (I);

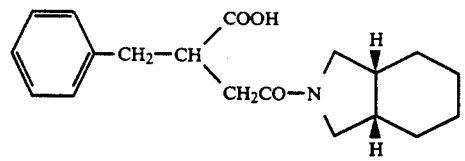

and enantiomers thereof and racemic mixtures thereofs and pharmaceutically acceptable salts thereof;

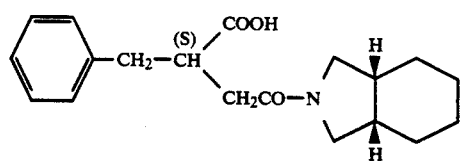

wherein C marked with (S) represents a carbon atom in S-configuration; and the pharmaceutically acceptable salts thereof.

BACKGROUND OF THE INVENTION

Diabetes is a sugar metabolic disorder disease mainly exhibiting hyperglycemia and shows symptoms of hunger, thirst and polyuria, and in the severe case causes coma.

For the prevention or treatment of diabetes, the dietetics, physical exercise, insulinization and oral administration of a hypoglycemic agent are being carried out generally.

At present sulfonylurea derivatives are the most widely prescribed drugs for the treatment of diabetes. Sulfonylurea derivatives possess a strong and prolonged hypoglycemic acitivity. On the other hand, they do have the disadvantages such as hypoglycemia and primary or secondary failure of efficacy. Therefore, it has been desired to develop more favorable drugs. The compounds of the present invention have a property that the glucose level after a meal is rapidly reduced, and thus are useful as a therapeutic agent for treatment of diabetes.

PRIOR ART

Benzylidenesuccinic acid compounds represented by the formula:

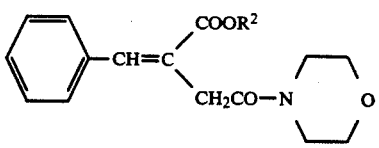

wherein $R^2$ represents a hydrogen atom, a methyl group and an ethyl group, have been disclosed in Journal of Medicinal Chemistry, Vol. 31, pages 2277–2288 (1988), Chemical Abstracts, Vol. 110, 24298u (1989), Vol. 114, 20680x (1991), Vol. 115, 136788p (1991); and the compound represented by the formula:

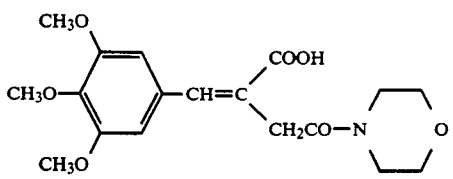

has been disclosed in Chemical Abstracts, Vol. 116, 42060p (1992).

Benzylsuccinic acid compounds represented by the formulae:

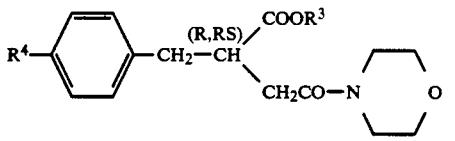

wherein $R^3$ represents a hydrogen atom, a methyl group, an ethyl group and a benzyl group; $R^4$ represents a hydrogen atom and a methoxy group; C marked with (R,RS) represents a carbon atom in R-configuration and RS-configuration; and

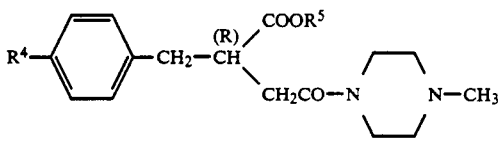

wherein $R^5$ represents a hydrogen atom and a benzyl group; C marked with (R) represents a carbon atom in R-configuration; $R^4$ has the same meaning as described above; and

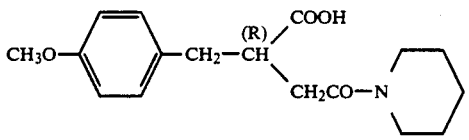

wherein C marked with (R) has the same meaning as described above, have been disclosed in Chemical Abstracts, Vol. 108, 205097g (1988), Vol. 110, 135731z, 24298u, 24311t, 39369s (1989), Vol. 111, 7784c, 195417g, 214942t (1989), Vol. 112, 7934x, 77963e, 178822p, 217541t, 217542u (1990), Vol. 113, 41323c, 59841e, 78956n (1990), Vol. 114, 102852u, 206805x (1991), Vol. 115, 136788p (1991), Vol. 116, 42060p (1992); and the compound represented by the formula:

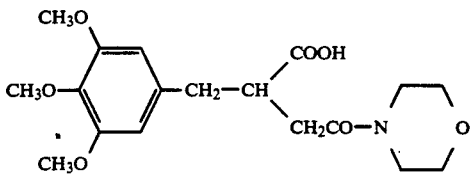

has been disclosed in Chemical Abstracts, Vol. 116, 42060p (1992).

These references report that these compounds are useful as intermediate materials in the preparation of a renin inhibitor, but there is no specific disclosure as to pharmacological activities themselves.

SUMMARY OF THE INVENTION

An object of the present invention is to provide novel succinic acid compounds and pharmaceutically acceptable salts thereof, which exhibit hypoglycemic activity.

Another object of the present invention is to provide pharmaceutical compositions containing a succinic acid compound or a pharmaceutically acceptable salt thereof as an active ingredient.

A further object of the present invention is to provide methods for the treatment of diabetes by administering a succinic acid compound or a pharmaceutically acceptable salt thereof.

Other objects, features and advantages of the present invention will become understood from the following description of the invention.

DETAILED DESCRIPTION OF THE INVENTION

The present invention provides succinic acid compounds which exhibit hypoglycemic activity.

The succinic acid compounds of the present invention enhance insulin secretion to reduce blood glucose levels.

Thus, the succinic acid compounds of the present invention are useful as hypoglycemic agents for the treatment of diabetes.

The term "alkyl group" used in the present invention means a straight or branched alkyl group.

The term "alkoxy group" used in the present invention means a straight or branched alkoxy group.

The term "aralkyl group" used in the present invention means a straight or branched alkyl group substituted by a phenyl group, such as benzyl, phenethyl, phenylpropyl, phenylbutyl and α-methylbenzyl.

The term "cycloalkyl group" used in the present invention means a 3 to 8-membered cycloalkyl group such as cyclopropyl, cyclobutyl, cyclopentyl, cyclohexyl, cycloheptyl and cyclooctyl.

The term "halogen atom" used in the present invention means a halogen atom such as chlorine, bromine, iodine and fluorine.

The term "heterocyclic group" used in the present invention means an aromatic monocyclic heterocyclic group such as thienyl, furyl and pyridyl.

The term "bicyclic amino group" used in the present invention means a bicyclic amino group which consists of a 5 or 6-membered cyclic amino ring fused with a 5 or 6-membered cycloalkyl ring, which may have 1 or 2 unsaturated bonds, such as cis-hexahydro-2-isoindolinyl, trans-hexahydro-2-isoindolinyl, 4,5,6,7-tetrahydro-2-isoindolinyl, trans-3a,4,7,7a-tetrahydro-2-isoindolinyl, cis-3a,4,7,7a-tetrahydro-2-isoindolinyl, 3a,4,5,7a-tetrahydro-2-isoindolinyl, 3a,7a-dihydro-2-isoindolinyl, trans-hexahydro-1-indolinyl, cis-hexahydro-1-indolinyl, trans-3a,4,7,7a-tetrahydro-1-indolinyl, cis-3a,4,7,7a-tetrahydro-1-indolinyl, 3a,6,7,7a-tetrahydro-1-indolinyl, 3a,7a-dihydro-1-indolinyl, cis-octahydro-2-pyrindin-2-yl, trans-octahydro-2-pyrindin-2-yl, cis-octahydro-1-pyrindin-1-yl, trans-octahydro-1-pyrindin-1-yl, cis-octahydro-1-cyclopenta[b]pyrrolyl, trans-octahydro-1-cyclopenta[b]pyrrolyl, cis-octahydro-2-cyclopenta[c]pyrrolyl, 1,2,3,4,5,6,7,8-octahydro-2-isoquinolyl, cis-1,2,3,4,4a,5,8,8a-octahydro-2-isoquinolyl, trans-1,2,3,4,4a5,8,8a-octahydro-2-isoquinolyl, trans-1,2,3,4,4a,7,8,8a-octahydro-2-isoquinolyl, trans- 1,2,3,4,4a,5,6,8a-octahydro-2-isoquinolyl, cis-decahydro-2-isoquinolyl, trans-decahydro2-isoquinolyl, 1,2,3,4,5,8-hexahydro-2-isoquinolyl, trans-decahydro-1-quinolyl, cis-decahydro-1-quinolyl, cis1,2,3,4,4a,5,6,8a-octahydro-1-quinolyl and 1,2,3,4,5,6,7,8-octahydro-1-quinolyl, and such a bicyclic amino group bonds to the carbon atom of the carbonyl group at the nitrogen atom of the cyclic amino ring.

The novel succinic acid compounds of the present invention, represented by the formula:

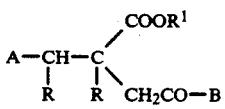
(I)

wherein A, B, R and $R^1$ have the same meanings as described above, can be prepared by reacting a succinic monoester compound represented by the formula:

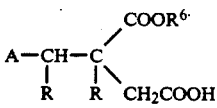
(II)

wherein $R^6$ represents a lower alkyl group or an aralkyl group; A and R have the same meanings as described above, with a bicyclic amino compound represented by the formula:

B—H (III)

wherein B has the same meaning as described above, and then, if desired, hydrolyzing or hydrogenolyzing the resulting compound.

Of the succinic acid compounds represented by the formula (I) of the present invention, the compounds wherein R combine with each other to form a chemical bond, represented by the formula:

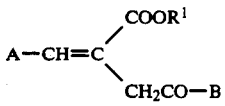
(Ia)

wherein A, B and $R^1$ have the same meanings as described above, can be also prepared by reacting an succinic anhydride compound represented by the formula:

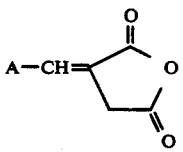
(IV)

wherein A has the same meaning as described above, with the bicyclic amino compound of the formula (III), and then, if desired, esterifying the resulting compound.

Of the succinic acid compounds represented by the formula (I) of the present invention, the compounds wherein R represents a hydrogen atom, represented by the formula:

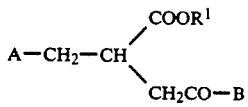
(Ib)

wherein A, B and $R^1$ have the same meanings as described above, can be prepared by reacting a succinic diester compound represented by the formula:

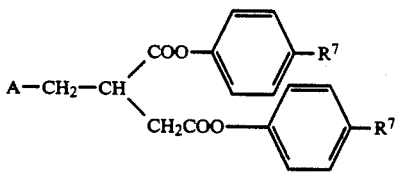
(V)

wherein $R^7$ represents a nitro group or a halogen atom; A has the same meaning as described above, with the bicyclic amino compound represented by the above formula (III), and by hydrolysis or alcoholysis of the obtained monoester compound represented by the formula:

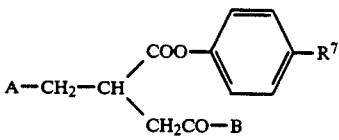
(VI)

wherein A, B and $R^7$ have the same meanings as described above, and then, if desired, esterifying the resulting carboxylic acid compound.

Furthermore, the compound (Ib) wherein B represents a saturated bicyclic amino group, can be also prepared by a reduction such as the catalytic hydrogenation, of the above corresponding compound (Ia), and then, if desired, esterifying the resulting carboxylic acid compound.

The succinic monoester compounds represented by the formula (II) used as starting materials in the present invention can be easily prepared by a method disclosed in literature, for example, Organic Reactions, Vol. 6, pages 1-73, Journal of Medicinal Chemistry, Vol. 31, pages 2277-2288 (1988) or by an analogous method thereto.

The bicyclic amino compounds represented by the formula (III) used as starting materials in the present invention are commercially available or can be easily prepared by a method disclosed in literature, for example, Journal of Organic Chemistry, Vol. 20, pages 1687-1694 (1955).

The succinic anhydride compounds represented by the formula (IV) used as starting materials in the present invention can be easily prepared by a method disclosed in literature, for example, Journal of the American Chemical Society, Vol. 74, pages 5147-5151 (1952), or by an analogous method thereto.

The succinic diester compounds represented by the formula (V) used as starting materials in the present invention can be easily prepared as follows. That is, a succinic acid compound represented by the formula:

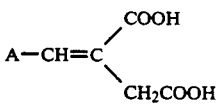

(VII)

wherein A has the same meaning as described above, which is obtained by a method disclosed in literature, for example, Organic Reactions, Vol. 6, pages 1-73 or by an analogous method thereto, is reduced to obtain a succinic acid compound represented by the formula:

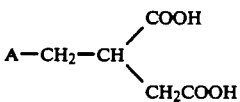

(VIII)

wherein A has the same meaning as described above, and then the obtained compound (VIII) is reacted with thionyl chloride and then with a phenol compound represented by the formula:

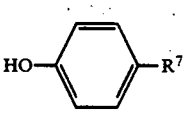

(IX)

wherein $R^7$ has the same meaning as described above, to obtain the above compound (V). The above succinic acid compounds (VIII) can be also prepared by a method disclosed in literature, for example, Journal of Organic Chemistry, Vol. 21, pages 1473-1477 (1956) or by an analogous method thereto.

The succinic acid compounds represented by the formula (I) of the present invention possess hypoglycemic activity at an oral dose of about 0.1 to 10 mg/kg in mouse or rat.

Among the succinic acid compounds represented by the formula (I) of the present invention, the preferred compounds are (E)-2-benzylidene-3-(cis-hexahydro-2-isoindolinylcarbonyl)propionic acid, (E)-2-benzylidene-3-(cis-3a,4,7,7a-tetrahydro-2-isoindolinylcarbonyl)-propionic acid, (E)-2-benzylidene-3-(trans-decahydro-2-isoquinolylcarbonyl)propionic acid, (E)-2-benzylidene-3-(trans-hexahydro-2-isoindolinylcarbonyl)propionic acid, (E)-2-(4-methylbenzylidene)-3-(cis-3a,4,7,7a-tetrahydro-2-isoindolinylcarbonyl)propionic acid, (E)-3-(cis-hexahydro-2-isoindolinylcarbonyl)-2-(2-methylbenzylidene)propionic acid, (E)-3-(cis-hexahydro-2-isoindolinylcarbonyl)-2-(2-isopropylbenzylidene)-propionic acid, (E)-2-(4-chlorobenzylidene)-3-(cis-hexahydro-2-isoindolinylcarbonyl)propionic acid, (E)-2-(2-fluorobenzylidene)-3-(cis-hexahydro-2-isoindolinylcarbonyl)propionic acid, (E)-2-(2-ethoxybenzylidene)-3-(cis-hexahydro-2-isoindolinylcarbonyl)propionic acid, (E)-2-(2,6-dichlorobenzylidene)-3-(cis-hexahydro-2-isoindolinylcarbonyl)propionic acid, (E)-3-(cis-hexahydro-2-isoindolinylcarbonyl)-2-(2-thenylidene)propionic acid, (E)-2-cyclohexylmethylene-3-(cis-hexahydro-2-isoindolinylcarbonyl)propionic acid, 2-benzyl-3-(transhexahydro-2-isoindolinylcarbonyl)propionic acid, 2-benzyl-3-(trans-hexahydro-1-indolinylcarbonyl)propionic acid, 2-benzyl-3-(cis-hexahydro-2-isoindolinylcarbonyl)-propionic acid, (S)-2-benzyl-3-(cis-hexahydro-2-isoindolinylcarbonyl)propionic acid, (R)-2-benzyl-3-(cis-hexahydro-2-isoindolinylcarbonyl)propionic acid, 2-benzyl-3-(cis-3a,4,7,7a-tetrahydro-2-isoindolinylcarbonyl)propionic acid, 3-(cis-hexahydro-2-isoindolinylcarbonyl)-2-(4-methylbenzyl)propionic acid, 3-(cis-hexahydro-2-isoindolinylcarbonyl)-2-(2-methyl-benzyl)propionic acid, 3-(cis-hexahydro-2-isoindolinylcarbonyl)-2-(2-methoxybenzyl)propionic acid, 3-(cis-hexahydro-2-isoindolinylcarbonyl)-2-(2-propoxybenzyl)-propionic acid, 2-(2,6-dimethylbenzyl)-3-(cis-hexa-hydro-2-isoindolinylcarbonyl)propionic acid, 3-(cis-hexahydro-2-isoindolinylcarbonyl)-2-(2-thenyl)-propionic acid and 2-cyclohexylmethyl-3-(cis-hexahydro-2-isoindolinylcarbonyl)propionic acid, and the most preferred compound is (S)-2-benzyl-3-(cis-hexahydro-2-isoindolinylcarbonyl)propionic acid.

In the succinic acid compounds (I) of the present invention, there are geometrical isomers, for example, when R combines each other to form a chemical bond, E-isomers and Z-isomers, when one or two bridgehead carbon atoms at the moiety of the bicyclic amino group don't form an unsaturated bond, cis-isomers and trans-isomers. All of isomers can be employed in the present invention. However, E-isomer is preferable than Z-isomer. That is, E-isomer tends to show a stronger stimulatory effect on insulin secretion and hypoglycemic activity.

In the succinic acid compounds (I) of the present invention, there are optical isomers, for example, when R represents a hydrogen atom, R-isomers and S-isomers. R-Isomer, S-isomer and a mixture of R-isomer and S-isomer can be employed in the present invention.

The compounds of the formula (I) in which $R^1$ is a hydrogen atom can be converted into pharmaceutically acceptable salts thereof according to the conventional methods. Examples of such pharmaceutically acceptable salts include alkaline metal salts such as sodium salts and potassium salts, alkaline earth metal salts such as calcium salts and magnesium salts and organic salts which are formed with organic amines such as morpholine, piperidine and phenylalaninol, or amino acids such as arginine. These pharmaceutically acceptable salts possess the same potency as the free carboxylic acid compounds, and thus they are useful as therapeutic agents for the treatment of diabetes.

When the succinic acid compounds of the formula (I) of the present invention or the pharmaceutically acceptable salts thereof are employed therapeutically, they can be administered in various dosage forms depending upon the intended therapy. Administration of the compound for such therapeutic purpose may be oral or parenteral, using appropriate dosage forms, e.g. tablets, pills, powders, granules, capsules and injectable preparations. These pharmaceutical compositions can be formulated in accordance with a conventional molding method.

In molding the pharmaceutical compositions into a tablet form, a wide variety of conventional carriers known in the art can be used. Examples of suitable carriers are excipients such as glucose, lactose, sucrose, partly pregelatinized starch, micro-crystalline cellulose and calcium hydrogenphosphate, binders such as hydroxypropylcellulose, polyvinylpyrrolidone and croscarmellose sodium, disintegrators such as carmellose calcium and low substituted hydroxypropylcellulose, and lubricants such as magnesium stearate, calcium stearate and talc. The tablets, if desired, can be coated and made into sugar-coated tablets, gelatin-coated tablets, enteric-coated tablets, film-coated tablets, or tablets coated with two or more layers.

When the pharmaceutical composition is formulated into an injectable preparation, the resulting solution and suspension are preferably sterilized, and are isotonic with respect to blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent in an amount sufficient to prepare an isotonic solution. The therapeutic agent may further contain ordinary dissolving aids, buffers, pain-alleviating agents, and preservatives, and optionally, coloring agents, fragrances, flavors, sweeteners, and other pharmacologically active agents which are known in the art.

The dosage of the succinic acid compounds of the present invention may be in the range from about 10 to 1000 mg per adult human by oral administration per day, or from about 1 to 100 mg per adult human by parenteral administration per day in multiple dose depending upon the type of disease, the severity of condition to be treated, and the like.

The present invention is further illustrated in more detail by way of the following Reference Examples, Examples and Test Examples. The melting points of the products obtained are uncorrected.

REFERENCE EXAMPLE 1

(E)-2-Methylbenzylidenesuccinic anhydride

To a solution of potassium t-butoxide (8.5 g) in t-butanol (100 ml) was added a mixture of 2-methylbenzaldehyde (6.0 g) and diethyl succinate (12.0 g) and the mixture was refluxed for 3 hours. After the solvent was evaporated under reduced pressure, 10% sodium hydroxide solution (100 ml) was added to the resulting residue and the mixture was refluxed for 5 hours. The reaction mixture was acidified with hydrochloric acid under ice-cooling and the precipitated crystals were collected by filtration to give 3.6 g of (E)-2-methylbenzylidenesuccinic acid.

(E)-2-Methylbenzylidenesuccinic acid (1.1 g) was added to acetic anhydride (20 ml) and the mixture was stirred at 60° C for 2 hours. After the solvent was evaporated under reduced pressure, the residue was recrystallized from toluene-hexane (1:5) to give 0.9 g of (E)-2-methylbenzylidenesuccinic anhydride.

Melting point: 112°–113° C.
NMR (CDCl$_3$, 400 MHz)
δ: 2.43(3H, s), 3.82(2H, d, J=2.6 Hz), 7.25–7.45(4H, m), 7.77(1H, t, J=2.6 Hz)
IR (KBr): νCO 1840, 1780 cm$^{-1}$

REFERENCE EXAMPLE 2

In a similar manner to that described in reference example 1, the following compound was prepared from 3-methylbenzaldehyde instead of 2-methylbenzaldehyde.

(E)-3-Methylbenzylidenesuccinic anhydride

Melting point: 117°–118° C.
NMR (CDCl$_3$, 270 MHz)
δ: 2.42(3H, s), 3.83(2H, d, J=2.2 Hz), 7.2–7.45(4H, m), 7.76(1H, t, J=2.2 Hz)
IR (KBr): νCO 1830, 1760 cm$^{-1}$

REFERENCE EXAMPLE 3

In a similar manner to that described in reference example 1, the following compound was prepared from 2-isopropylbenzaldehyde instead of 2-methylbenzaldehyde.

(E)-2-Isopropylbenzylidenesuccinic anhydride

Melting point: 110°–111° C.
NMR (CDCl$_3$, 400 MHz)
δ: 1.27(6H, d, J=6.8 Hz), 3.2–3.35(1H, m), 3.76 (2H, d, J=2.6 Hz), 7.25–7.5(4H, m), 8.17(1H, t, J=2.6 Hz)
IR (KBr): νCO 1850, 1780 cm$^{-1}$

REFERENCE EXAMPLE 4

In a similar manner to that described in reference example 1, the following compound was prepared from 2-fluorobenzaldehyde instead of 2-methylbenzaldehyde.

(E)-2-Fluorobenzylidenesuccinic anhydride

Melting point: 154°–155° C.
NMR (CDCl$_3$, 270 MHz)
δ: 3.92(2H, d, J=2.5 Hz), 7.15–7.65(4H, m), 7.89 (1H, t, J=2.5 Hz)
IR (KBr): νCO 1840, 1770 cm$^{-1}$

REFERENCE EXAMPLE 5

In a similar manner to that described in reference example 1, the following compound was prepared from 2-ethoxybenzaldehyde instead of 2-methylbenzaldehyde.

(E)-2-Ethoxybenzylidenesuccinic anhydride

Melting point: 137°–139° C.
NMR (CDCl$_3$, 400 MHz)
δ: 1.48(3H, t, J=7.0 Hz), 3.77(2H, d, J=2.6 Hz), 4.14(2H, q, J=7.0 Hz), 6.95–7.5(4H, m), 8.24 (1H, t, J=2.6 Hz)
IR (KBr): νCO 1840, 1770 cm$^{-1}$

REFERENCE EXAMPLE 6

In a similar manner to that described in reference example 1, the following compound was prepared from 2-propoxybenzaldehyde instead of 2-methylbenzaldehyde.

(E)-2-Propoxybenzylidenesuccinic anhydride

Melting point: 108°–109° C.
NMR (CDCl$_3$, 400 MHz)
δ: 1.0°–1.15(3H, m), 1.8°–1.95(2H, m), 3.77(2H, d, J=2.6 Hz), 3.95°–4.05(2H, m), 6.9°–7.5(4H, m), 8.25(1H, t, J=2.6 Hz)
IR (KBr): νCO 1830, 1770 cm$^{-1}$

REFERENCE EXAMPLE 7

In a similar manner to that described in reference example 1, the following compound was prepared from 2,6-dimethylbenzaldehyde instead of 2-methylbenzaldehyde.

(Z)-2,6-Dimethylbenzylidenesuccinic anhydride

Melting point: 159°–161° C.
NMR (CDCl$_3$, 400 MHz)
δ: 2.21(6H, s), 3.79(2H, d, J=2.3 Hz), 7.07(2H, d, J=7.6 Hz), 7.18(1H, t, J=7.6 Hz), 7.29(1H, t, J=2.3 Hz)
IR (KBr): νCO 1850, 1830, 1770 cm$^{-1}$

REFERENCE EXAMPLE 8

In a similar manner to that described in reference example 1, the following compound was prepared from 2,6-dichlorobenzaldehyde instead of 2-methylbenzaldehyde.

(E)-2,6-Dichlorobenzylidenesuccinic anhydride

Colorless amorphous solid
NMR (CDCl$_3$, 400 MHz)
δ: 3.55(2H, d, J=2.8 Hz), 7.1–7.45(3H, m), 7.80(1H, t, J=2.8 Hz)
IR (KBr): νCO 1840, 1780 cm$^{-1}$

REFERENCE EXAMPLE 9

In a similar manner to that described in reference example 1, the following compound was prepared from 2,6-dimethoxybenzaldehyde instead of 2-methylbenzaldehyde.

(E)-2,6-Dimethoxybenzylidenesuccinic anhydride

Melting point: 167°–168° C.
NMR (CDCl$_3$, 400 MHz)
δ: 3.55(2H, d, J=2.7 Hz), 3.88(6H, s), 6.60(2H, d, J=8.4 Hz), 7.39(1H, t, J=8.4 Hz), 7.99(1H, t, J=2.7 Hz)
IR (KBr): νCO 1840, 1770 cm$^{-1}$

REFERENCE EXAMPLE 10

In a similar manner to that described in reference example 1, the following compound was prepared from cyclohexanecarbaldehyde instead of 2-methylbenzaldehyde.

(E)-Cyclohexylmethylenesuccinic anhydride

Melting point: 79°–80° C.
NMR (CDCl$_3$, 270 MHz)
δ: 1.1–1.45(5H, m), 1.55–1.9(5H, m), 2.1–2.3(1H,
IR (KBr): νCO 1830, 1770 cm$^{-1}$

REFERENCE EXAMPLE 11

(E)-3-Methoxycarbonyl-4-(3-methylphenyl)-3-butenoic acid

To a solution of sodium methoxide (1.4 g) in methanol (20 ml) was added a mixture of 3-methylbenzaldehyde (2.4 g) and dimethyl succinate (3.5 g) and the mixture was refluxed for 3 hours. After the reaction mixture was concentrated in vacuo, water was added to the resulting residue and the mixture was washed with diethyl ether. The aqueous layer was acidified with hydrochloric acid and extracted with diethyl ether. The organic layer was washed with brine and dried over MgSO$_4$. The solvent was evaporated under reduced pressure to give 3.8 g of (E)-3-methoxycarbonyl-4-(3-methylphenyl)-3-butenoic acid as a pale yellow viscous oil.

NMR (CDCl$_3$, 270 MHz)
δ: 2 37(3H, s), 3.59(2H, s), 3.84(3H, s), 7.0–7.4(4H, m), 7.90(1H, s), 9.90(1H, bs)
IR (neat): νCO 1730, 1710, 1650, 1610 cm$^{-1}$

REFERENCE EXAMPLE 12

Di(4-nitrophenyl) 2-(4-methylbenzyl)succinate

To a suspension of 2-(4-methylbenzylidene)succinic acid (4.5 g) in ethanol (50 ml) was added 10% Pd-C (100 mg) and the mixture was hydrogenated at room temperature and atmospheric pressure for 40 hours. After the catalyst was filtered off, the solvent was evaporated under reduced pressure. The resulting residue was recrystallized from hexane-ethyl acetate (1:1) to give 4.3 g of 2-(4-methylbenzyl)succinic acid.

To 2-(4-methylbenzyl)succinic acid (2.2 g) were added thionyl chloride (7.0 ml) and N,N-dimethylformamide (0.5 ml) and the mixture was stirred at 80° C. for 2 hours. The excess thionyl chloride was evaporated under reduced pressure and dichloromethane (30 ml) was added to the residue. To the mixture were added 4-nitrophenol (3.0 g) and triethylamine (4.0 g) with stirring at 0° C.. After stirring at room temperature for 16 hours, the reaction mixture was washed successively with 1N hydrochloric acid, saturated sodium bicarbonate solution, and brine and dried over MgSO$_4$. After the solvent was evaporated under reduced pressure, the residue was purified by column chromatography on silica gel eluting with hexane/ethyl acetate (4/1) to give 2.4 g of di(4-nitrophenyl) 2-(4-methylbenzyl)succinate.

Melting point: 97°–98° C.
NMR (CDCl$_3$, 400 MHz)
δ: 2.37(3H, s), 2.8–3.3(4H, m), 3.4–3.55(1H, m), 7.1–7.3(8H, m), 8.2–8.3(4H, m)
IR (KBr): νCO 1750 cm$^{-1}$.
νNO$_2$ 1530 cm$^{-1}$

EXAMPLE 1

(E)-2-Benzylidene-3-(cis-hexahydro-2-isoindolinylcarbonyl)propionic acid

To a suspension of (E)-benzylidenesuccinic anhydride (13.9 g) in dichloromethane (120 ml) was added cis-hexahydroisoindoline (12.0 g) and the mixture was stirred at room temperature for 2 hours. The reaction mixture was washed successively with 1N hydrochloric acid and brine and dried over MgSO$_4$. After the solvent was evaporated under reduced pressure, the residue was crystallized from ethyl acetate to give 19.5 g of (E)-2-benzylidene-3-(cis-hexahydro-2-isoindolinylcarbonyl)propionic acid.

Melting point: 154°–156° C.
NMR (DMSO-d$_6$, 400 MHz)
δ: 1.3–1.65(8H, m), 2.1–2.35(2H, m), 3.2–3.55(6H, m), 7.35–7.5(5H, m), 7.75(1H, s), 12.55(1H, bs)
IR (KBr): νCO 1700, 1600 cm$^{-1}$

EXAMPLE 2

In a similar manner to that described in example 1, the following compound was prepared from cis-3a,4,7,7a-tetrahydroisoindoline instead of cis-hexahydroisoindoline.

(E)-2-Benzylidene-3-(cis-3a,4,7,7a-tetrahydro-2-isoindolinylcarbonyl)propionic acid Melting point: 150°–151° C.
NMR (DMSO-d$_6$, 400 MHz)
δ: 1.8–1.95(2H, m), 2.15–2.45(4H, m), 3.15–3.7 (6H, m), 5.6–5.75(2H, m), 7.35–7.45(5H, m), 7.55(1H, s), 12.55(1H, bs)
IR (KBr): νCO 1700, 1600 cm$^{-1}$

EXAMPLE 3

In a similar manner to that described in example 1, the following compound was prepared from trans-decahydroisoquinoline instead of cis-hexahydroisoindoline.

(E)2-Benzylidene-3-(trans-decahydro-2-isoquinolylcarbonyl)propionic acid

Melting point: 125°–126° C.
NMR (DMSO-d$_6$, 270 MHz)
δ: 0.9–1.5(7H, m), 1.6–1.9(5H, m), 2.2–3.5(2H, m), 3.55(2H, s), 3.8–4.7(2H, m), 7.4–7.65(5H, m), 7.83(1H, s), 12.55(1H, bs)
IR (KBr): νCO 1680, 1635 cm$^{-1}$

EXAMPLE 4

In a similar manner to that described in example 1, the following compound was prepared from trans-hexahydroindoline instead of cis-hexahydroisoindoline.

(E)-2-Benzylidene-3-(trans-hexahydro-1-indolinylcarbonyl)propionic acid

Colorless amorphous solid
NMR (DMSO-$d_6$, 270 MHz)
δ: 1.15-2.5(11H, m), 3.3-3.8(4H, m), 3.9-4.1(1H, m), 7.4-7.65(5H, m), 7.88(1H, d, J=1.5 Hz), 12.60(1H, bs)
IR (KBr): νCO 1710, 1635, 1605 cm$^{-1}$

EXAMPLE 5

In a similar manner to that described in example 1, the following compound was prepared from trans-hexahydroisoindoline instead of cis-hexahydroisoindoline.

(E)-2-Benzylidene-3-(trans-hexahydro-2-isoindolinylcarbonyl)propionic acid

Melting point: 169°-171° C.
NMR (DMSO-$d_6$, 270 MHz)
δ: 1.0-1.95(10H, m), 2.65-3.05(2H, m), 3.2-3.75(4H, m), 7.3-7.5(5H, m), 7.72(1H, s), 12.49(1H, s)
IR (KBr): νCO 1715, 1650, 1600 cm$^{-1}$

EXAMPLE 6

In a similar manner to that described in example 1, the following compound was prepared from (E)-4-methylbenzylidenesuccinic anhydride and cis-3a,4,7,7a-tetrahydroisoindoline instead of
(E)-benzylidenesuccinic anhydride and cis-hexahydroisoindoline.

(E)-2-(4-Methylbenzylidene)-3-(cis-3a,4,7,7a-tetrahydro-2-isoindolinylcarbonyl)propionic acid Melting point: 152°-153° C.
NMR (CDCl$_3$, 400 MHz)
δ: 1.85-1.95(2H, m), 2.2-2.5(7H, m), 3.15-3.25(1H, m), 3.35-3.65(5H, m), 5.6-5.75(2H, m), 7.15-7.3(4H, m), 7.86(1H, s)
IR (KBr): νCO 1710, 1650, 1600 cm$^{-1}$

EXAMPLE 7

In a similar manner to that described in example 1, the following compound was prepared from (E)-3-methylbenzylidenesuccinic anhydride and cis-3a,4,7,7a-tetrahydroisoindoline instead of
(E)-benzylidenesuccinic anhydride and cis-hexahydroisoindoline.

(E)-2-(3-Methylbenzylidene)-3-(cis-3a,4,7,7a-tetrahydro-2-isoindolinylcarbonyl)propionic acid Melting point: 141°-143° C.
NMR (CDCl$_3$, 270 MHz)
δ: 1.8-2.0(2H, m), 2.15-2.55(7H, m), 3.05-3.25(1H, m), 3.3-3.65(5H, m), 5.55-5.8(2H, m), 7.05-7.35(4H, m), 7.84(1H, s)
IR (KBr): νCO 1710, 1650, 1630, 1610 cm$^{-1}$

EXAMPLE 8

In a similar manner to that described in example 1, the following compound was prepared from (E)-4-methoxybenzylidenesuccinic anhydride and cis-3a,4,7,7a-tetrahydroisoindoline instead of
(E)-benzylidenesuccinic anhydride and cis-hexahydroisoindoline.

(E)-2-(4-Methoxybenzylidene)-3-(cis-3a,4,7,7a-tetrahydro-2-isoindolinylcarbonyl)propionic acid Melting point: 158°-160° C.
NMR (DMSO-$d_6$, 270 MHz)
δ: 1.75-1.95(2H, m), 2.1-2.5(4H, m), 3.1-3.45(5H, m), 3.55-3.7(1H, m), 3.78(3H, s), 5.6-5.75(2H, m), 6.9-7.45(4H, m), 7.68(1H, s), 12.36(1H, bs)
IR (KBr): νCO 1710, 1610 cm$^{-1}$

EXAMPLE 9

In a similar manner to that described in example 1, the following compound was prepared from (E)-4-methylbenzylidenesuccinic anhydride instead of (E)-benzylidenesuccinic anhydride.

(E)-3-(cis-Hexahydro-2-isoindolinylcarbonyl)-2-(4-methylbenzylidene)propionic acid Melting point: 173°-175° C.
NMR (CDCl$_3$, 400 MHz)
δ: 1.35-1.7(8H, m), 2.2-2.35(2H, m), 2.37(3H, s), 3.25-3.35(1H, m), 3.4-3.6(5H, m), 7.15-7.3(4H, m), 7.87(1H, s)
IR (KBr): νCO 1710, 1650, 1600 cm$^{-1}$

EXAMPLE 10

In a similar manner to that described in example 1, the following compound was prepared from (E)-2-methylbenzylidenesuccinic anhydride instead of (E)-benzylidenesuccinic anhydride.

(E)-3-(cis-Hexahydro-2-isoindolinylcarbonyl)-2-(2-methylbenzylidene)propionic acid Melting point: 154°-156° C.
NMR (CDCl$_3$, 270 MHz)
δ: 1.25-1.7(8H, m), 2.1-2.35(5H, m), 2.9-3.55(6H, m), 7.1-7.35(4H, m), 7.85(1H, s)
IR (KBr): νCO 1710, 1650, 1600 cm$^{-1}$

EXAMPLE 11

In a similar manner to that described in example 1, the following compound was prepared from (E)-2-isopropylbenzylidenesuccinic anhydride instead of (E)-benzylidenesuccinic anhydride.

(E)-3-(cis-Hexahydro-2-isoindolinylcarbonyl)-2-(2-isopropylbenzylidene)propionic acid Melting point: 172°-173° C.
NMR (CDCl$_3$, 270 MHz)
δ: 1.1-1.7(14H, m), 2.1-2.3(2H, m), 2.9-3.15(3H, s)
IR (KBr): νCO 1680, 1640 cm$^{-1}$

EXAMPLE 12

In a similar manner to that described in example 1, the following compound was prepared from (E)-4-chlorobenzylidenesuccinic anhydride instead of (E)-benzylidenesuccinic anhydride.

(E)-2-(4-Chlorobenzylidene)-3-(cis-hexahydro-2-isoindolinylcarbonyl)propionic acid Melting point: 172°-174° C.
NMR (CDCl$_3$, 270 MHz)

δ: 1.3-1.7(8H, m), 2.15-2.4(2H, m), 3.2-3.6(6H, m), 7.25-7.45(4H, m), 7.85(1H, s)
IR (KBr): νCO 1710, 1650, 1590 cm⁻¹

EXAMPLE 13

In a similar manner to that described in example 1, the following compound was prepared from (E)-2-chlorobenzylidenesuccinic anhydride instead of (E)-benzylidenesuccinic anhydride.

(E)-2-(2-Chlorobenzylidene)-3-(cis-hexahydro-2-isoindolinylcarbonyl)propionic acid Melting point: 180°-181° C.
NMR (DMSO-d₆, 270 MHz)
δ: 1.15-1.65(8H, m), 2.05-2.35(2H, m), 3.05-3.55(6H, m), 7.3-7.65(4H, m), 7.74(1H, s), 12.73(1H, bs)
IR (KBr): νCO 1710, 1650, 1600 cm⁻¹

EXAMPLE 14

In a similar manner to that described in example 1, the following compound was prepared from (E)-2-fluorobenzylidenesuccinic anhydride instead of (E)-benzylidenesuccinic anhydride.

(E)-2-(2-Fluorobenzylidene)-3-(cis-hexahydro-2-isoindolinylcarbonyl)propionic acid Melting point: 172°-173° C.
NMR (CDCl₃, 400 MHz)
δ: 1.3-1.7(8H, m), 2.15-2.35(2H, m), 3.2-3.6(6H, m), 7.05-7.55(4H, m), 7.86(1H, s), 12.9(1H, br)
IR (KBr): νCO 1700, 1600 cm⁻¹

EXAMPLE 15

In a similar manner to that described in example 1, the following compound was prepared from (E)-2-methoxybenzylidenesuccinic anhydride instead of (E)-benzylidenesuccinic anhydride.

(E)-3-(cis-Hexahydro-2-isoindolinylcarbonyl)-2-(2-methoxybenzylidene)propionic acid Melting point: 148°-149° C.
NMR (CDCl₃, 270 MHz)
δ: 1.3-1.7(8H, m), 2.15-2.35(2H, m), 3.15-3.55(6H, m), 3.83(3H, s), 6.85-7.4(4H, m), 7.97 (1H, s), 12.1(1H, br)
IR (KBr): νCO 1710, 1600 cm⁻¹

EXAMPLE 16

In a similar manner to that described in example 1, the following compound was prepared from (E)-2-ethoxybenzylidenesuccinic anhydride instead of (E)-benzylidenesuccinic anhydride.

(E)-2-(2-Ethoxybenzylidene)-3-(cis-hexahydro-2-isoindolinylcarbonyl)propionic acid Melting point: 128°-130° C.
NMR (CDCl₃, 400 MHz)
δ: 1.2-1.65(11H, m), 2.1-2.25(2H, m), 3.05-3.2 (1H, m), 3.25-3.55(5H, m), 4.02(2H, q, J=7.0 Hz), 6.8-7.3(4H, m), 7.88(1H, s), 10.0(1H, br)
IR (KBr): νCO 1700, 1650, 1610 cm⁻¹

EXAMPLE 17

In a similar manner to that described in example 1, the following compound was prepared from (E)-2-propoxybenzylidenesuccinic anhydride instead of (E)-benzylidenesuccinic anhydride.

(E)-3-(cis-Hexahydro-2-isoindolinylcarbonyl)-2-(2-propoxybenzylidene)propionic acid Melting point: 138°-139° C.
NMR (CDCl₃, 400 MHz)
δ: 0.95-1.05(3H, m), 1.2-1.65(8H, m), 1.7-1.85(2H, m), 2.05-2.25(2H, m), 3.05-3.15(1H, m), 3.25-3.55(5H, m), 3.85-3.95(2H, m), 6.8-7.35(4H, m), 7.89(1H, s)
IR (KBr): νCO 1700, 1650, 1610 cm⁻¹

EXAMPLE 18

In a similar manner to that described in example 1, the following compound was prepared from (Z)-2,6-dimethylbenzylidenesuccinic anhydride instead of (E)-benzylidenesuccinic anhydride.

(Z)-2-(2,6-Dimethylbenzylidene)-3-(cis-hexahydro-2-isoindolinylcarbonyl)propionic acid Melting point: 171°-172° C.
NMR (CDCl₃, 400 MHz)
δ: 1.35-1.7(8H, m), 2.24(6H, s), 2.25-2.4(2H, m), 3.4-3.65(6H, m), 6.74(1H, s), 6.95-7.1(3H, m)
IR (KBr): νCO 1730, 1610 cm⁻¹

EXAMPLE 19

In a similar manner to that described in example 1, the following compound was prepared from (E)-2,6-dichlorobenzylidenesuccinic anhydride instead of (E)-2,6-dichlorobenzylidenesuccinic anhydride instead of (E)-benzylidenesuccinic anhydride.

(E)-2-(2,6-Dichlorobenzylidene)-3-(cis-hexahydro-2-isoindolinylcarbonyl)propionic acid Melting point: 263°-265° C.
NMR (DMSO-d₆, 400 MHz)
δ1.1-1.65(8H, m), 2.0-2.35(2H, m), 3.0-3.5(6H, m),7.3-7.65(4H, m), 12.7(1H, br)
IR (KBr): νCO 1715, 1650, 1600 cm⁻¹

EXAMPLE 20

In a similar manner to that described in example 1, the following compound was prepared from (E)-2,6-dimethoxybenzylidenesuccinic anhydride instead of (E)-benzylidenesuccinic anhydride.

(E)-2-(2,6-Dimethoxybenzylidene)-3-(cis-hexahydro-2-isoindolinylcarbonyl)propionic acid Melting point: 174°-175° C.
NMR (CDCl₃, 270 MHz)
δ: 1.25-1.7(8H, m), 2.1-2.3(2H, m), 2.9-3.55(6H, m), 3.75(6H, s), 6.5-6.6(2H, m), 7.2-7.35(1H, m), 7.51(1H, s), 13.8(1H, br)
IR (KBr): νCO 1710, 1640, 1590 cm⁻¹

EXAMPLE 21

In a similar manner to that described in example 1, the following compound was prepared from (E)-2-thenylidenesuccinic anhydride instead of (E)-benzylidenesuccinic anhydride.

(E)-3-(cis-Hexahydro-2-isoindolinylcarbonyl)-2-(2-thenylidene)propionic acid

Melting point: 142°-143° C.
NMR (CDCl₃, 270 MHz)
δ: 1.3-1.75(8H, m), 2.15-2.45(2H, m), 3.35-3.75(6H, m), 6.9(1H, br), 7.05-7.15(1H, m), 7.31(1H, d, J=3.3 Hz), 7.46(1H, d, J=4.9 Hz), 8.04(1H, s)

IR (KBr): νCO 1710, 1650, 1600 cm⁻¹

EXAMPLE 22

In a similar manner to that described in example 1, the following compound was prepared from (E)-cyclohexylmethylenesuccinic anhydride instead of (E)-benzylidenesuccinic anhydride.

(E)-2-Cyclohexylmethylene-3-(cis-hexahydro-2-isoindolinylcarbonyl)propionic acid Melting point: 168°-169° C.
NMR (CDCl₃, 400 MHz)
δ: 1.1-1.9(18H, m), 2.15-2.4(3H, m), 3.2-3.65(6H, m), 6.79(1H, d, J=10.0 Hz), 10.8(1H, br)
IR (KBr): νCO 1715, 1600 cm⁻¹

EXAMPLE 23

(Z)-2-Benzylidene-3-(cis-hexahydro-2-isoindolinylcarbonyl)propionic acid

To a suspension of (Z)-benzylidenesuccinic anhydride (139 mg) in dichloromethane (30 ml) was added cis-hexahydroisoindoline (120 mg) and the mixture was stirred at room temperature for 2 hours. To the reaction mixture was added 2N sodium hydroxide solution and the mixture was extracted with diethyl ether. The aqueous layer was acidified with 1N hydrochloric acid and extracted with dichloromethane. The organic layer was washed with brine and dried over MgSO₄. After the solvent was evaporated under reduced pressure, the residue was crystallized from ethyl acetate to give 190 mg of (Z)-2-benzylidene-3-(cis-hexahydro-2-isoindolinylcarbonyl)propionic acid.

Melting point: 126°-128° C.
NMR (DMSO-d₆, 400 MHz)
δ: 1.35-1.75(8H, m), 2.2-2.45(2H, m), 3.35-3.65(6H, m), 6.57(1H, s), 7.2-7.5(5H, m), 13.65(1H, bs)
IR (KBr): νCO 1730, 1580 cm⁻¹

EXAMPLE 24

Sodium (E)-2-benzylidene-3-(cis-hexahydro-2-isoindolinylcarbonyl)propionate

To a solution of (E)-2-benzylidene-3-(cis-hexahydro-2-isoindolinylcarbonyl)propionic acid (31 mg) in ethanol (0.3 ml) was added 1N sodium hydroxide solution (0.1 ml) and the mixture was stirred at room temperature for 2 hours. The solvent was evaporated under reduced pressure to give 30 mg of sodium (E)-2-benzylidene-3-(cis-hexahydro-2-isoindolinylcarbonyl)propionate as a colorless amorphous solid.

NMR (DMSO-d₆, 270 MHz)
δ: 1.2-1.65(8H, m), 2.0-2.3(2H, m), 3.1-3.65(6H, m), 7.2-7.5(6H, m)
IR (KBr): νCO 1630, 1570 cm⁻¹

EXAMPLE 25

In a similar manner to that described in example 24, the following compound was prepared from (E)-2-benzylidene-3-(cis-3a,4,7,7a-tetrahydro-2-isoindolinylcarbonyl)propionic acid instead of (E)-2-benzylidene-3-(cis-hexahydro-2-isoindolinylcarbonyl)propionic acid.

Sodium (E)-2-benzylidene-3-(cis-3a,4,7,7a-tetrahydro-2-isoindolinylcarbonyl)propionate Colorless amorphous solid
NMR (DMSO-d₆, 270 MHz)
δ: 1.75-1.95(2H, m), 2.1-2.4(4H, m), 3.05-3.15(1H, m), 3.2-3.45(4H, m), 3.6-3.75(1H, m), 5.55-5.75(2H, m), 7.15-7.5(6H, m)
IR (KBr): νCO 1625, 1570 cm⁻¹

EXAMPLE 26

Methyl (E)-2-benzylidene-3-(cis-hexahydro-2-isoindolinylcarbonyl)propionate

To a solution of (E)-2-benzylidene-3-(cis-hexahydro-2-isoindolinylcarbonyl)propionic acid (50 mg) in diethyl ether was added a solution of diazomethane in diethyl ether with stirring and the mixture was stirred at room temperature for 2 hours. The solvent was evaporated under reduced pressure to give 52 mg of methyl (E)-2-benzylidene-3-(cis-hexahydro-2-isoindolinylcarbonyl)propionate as a colorless viscous oil.

NMR (DMSO-d₆, 400 MHz)
δ: 1.25-1.6(8H, m), 2.1-2.3(2H, m), 3.2-3.55(6H, m), 3.72(3H, s), 7.35-7.5(5H, m), 7.76(1H, s)
IR (neat): νCO 1715, 1650 cm⁻¹

EXAMPLE 27

In a similar manner to that described in example 26 the following compound was prepared from (E)- 2-benzylidene-3-(cis-3a,4,7,7a-tetrahydro-2-isoindolinylcarbonyl)propionic acid instead of (E)-2-benzylidene3-(cis-hexahydro-2-isoindolinylcarbonyl)propionic acid.

Methyl (E)-2-benzylidene-3-(cis-3a,4,7,7a-tetrahydro-2-isoindolinylcarbonyl)propionate Colorless viscous oil
NMR (DMSO-d₆, 400 MHz)
δ: 1.8-1.95(2H, m), 2.15-2.5(4H, m), 3.1-3.65(6H, m), 3.74(3H, s), 5.6-5.75(2H, m), 7.35-7.5(5H, m), 7.78(1H, s)
IR (neat): νCO 1715, 1650 cm⁻¹

EXAMPLE 28

Methyl (E)-2-(3-methylbenzylidene)-3-(cis-3a,4,7,7a-tetrahydro-2-isoindolinylcarbonyl)propionate To a solution of (E)-3-methoxycarbonyl-4-(3-methylphenyl)-3-butenoic acid (1.05 g) in anhydrous tetrahydrofuran (20 ml) were added N-methylmorpholine (0.74 ml) and isobutyl chloroformate (0.75 ml) with stirring at −20° C. and the mixture was stirred for 20 minutes. To the mixture was added a solution of cis-3a,4,7,7a-tetrahydroisoindoline (773 mg) in anhydrous tetrahydrofuran (2 ml) with stirring at −20° C. After 1 hour, the deposit was filtered off and the solvent was evaporated under reduced pressure. The residue was dissolved in ethyl acetate and washed successively with 1N hydrochloric acid, saturated sodium bicarbonate solution, and brine and dried over MgSO₄. After the solvent was evaporated under reduced pressure, the residue was purified by column chromatography on silica gel eluting with hexane/ethyl acetate (4/1) to give 446 mg of methyl (E)-2-(3-methylbenzylidene)-3-(cis-3a,4,7,7a-tetrahydro-2-isoindolinylcarbonyl)propionate as a colorless viscous oil.

NMR (CDCl₃, 270 MHz)

δ: 1.85-2.05(2H, m), 2.2-2.55(7H, m), 3.25 3.65(6H, m), 3.81(3H, s), 5.55-5.75(2H, m), 7.1-7.35(4H, m), 7.88(1H, s)

IR (neat): νCO 1720, 1650 cm⁻¹

EXAMPLE 29

Methyl (E)-2-(4-methoxybenzylidene)-3-(cis-3a,4,7,7a-tetrahydro-2-isoindolinylcarbonyl)propionate To a suspension of (E)-2-(4-methoxybenzylidene)-3-(cis-3a,4,7,7a-tetrahydro-2-isoindolinycarbonyl)-propionic acid (50 mg) in diethyl ether (5 ml) was added a solution of diazomethane in diethyl ether (2 ml) with stirring at 0° C. After the mixture was stirred at room temperature for 1 hour, excess diazomethane was decomposed with acetic acid. The reaction mixture was washed successively with saturated sodium bicarbonate solution and water and dried over MgSO₄. After the solvent was evaporated under reduced pressure, the residue was purified by column chromatography on silica gel eluting with hexane/ethyl acetate (4/1) to give 51 mg of methyl (E)-2-(4-methoxybenzylidene)-3-(cis-3a,4,7,7a-tetrahydro-2-isoindolinylcarbonyl)propionate as a colorless viscous oil.

NMR (CDCl₃, 270 MHz)

δ: 1.85-2.05(2H, m), 2.2-2.55(4H, m), 3.25-3.7(6H, m), 3.79(3H, s), 3.82(3H, s), 5.6-5.75(2H, m), 6.85-7.5(4H, m), 7.87(1H, s)

IR (neat): νCO 1720, 1650 1610 cm⁻¹

EXAMPLE 30

In a similar manner to that described in example 29, the following compound was prepared from (E)-3-(cis-hexahydro-2-isoindolinylcarbonyl)-2-(2-methylbenzylidene)propionic acid instead of (E)-2-(4-methoxybenzylidene)-3-(cis-3a,4,7,7a-tetrahydro-2-isoindolinylcarbonyl)propionic acid.

Methyl (E)-3-(cis-hexahydro-2-isoindolinylcarbonyl)-2-(2-methylbenzylidene)propionate Colorless viscous oil NMR (CDCl₃, 270 MHz)

δ: 1.3-1.7(8H,m), 2.1-2.4(5H, m), 3.25-3.55(6H, m), 3.82(3H, s), 7.1-7.45(4H, m), 7.92(1H, s)

IR (neat): νCO 1720, 1650 cm⁻¹

EXAMPLE 31

In a similar manner to that described in example 29, the following compound was prepared from (E)-2-(4-chlorobenzylidene)-3-(cis-hexahydro-2-isoindolinylcarbonyl)propionic acid instead of (E)-2-(4-methoxybenzylidene)-3-(cis-3a,4,7,7a-tetrahydro-2-isoindolinylcarbonyl)propionic acid.

Methyl (E)-2-(4-chlorobenzylidene)-3-(cis-hexahydro-2-isoindolinylcarbonyl)propionic Colorless viscous oil NMR (CDCl₃, 270 MHz)

δ: 1.3-1.75(8H, m), 2.15-2.4(2H, m), 3.35-3.6(6H, m), 3.81(3H, s), 7.3-7.45(4H, m), 7.86(1H, s)

IR (neat): νCO 1720, 1650 cm⁻¹

EXAMPLE 32

Benzyl (E)-2-bensylidene-3-(cis-hexahydro-2-isoindolinylcarbonyl)propionic

To a solution of (E)-2-benzylidene-3-(cis-hexahydro-2-isoindolinylcarbonyl)propionic acid (50 mg) in dichloromethane (1 ml) were added triethylamine (23 μl) and benzyl bromide (19 μl) with stirring and the mixture was stirred at room temperature for 16 hours. To the reaction mixture was added dichloromethane. The mixture was washed successively with 1N hydrochloric acid, saturated sodium bicarbonate solution, and brine and dried over MgSO₄. The solvent was evaporated under reduced pressure to give 51 mg of benzyl (E)-2-benzylidene-3-(cis-hexahydro-2-isoindolinylcarbonyl)-propionate as a colorless viscous oil.

NMR (CDCl₃ 270 MHz)

δ: 1.25-1.65(8H, m), 2.1-2.3(2H, m), 3.25-3.55(6H, m), 5.23, 5.25(AB-q, 2H, J=12.9 Hz), 7.3-7.5(10H, m), 7.97(1H, s)

IR (neat): νCO 1715, 1650 cm⁻¹

EXAMPLE 33

In a similar manner to that described in example 32, the following compound was prepared from propyl bromide instead of benzyl bromide.

Propyl (E)-2-benzylidene-3-(cis-hexahydro-2-isoindolinylcarbonyl)propionate

Colorless viscous oil

NMR (CDCl₃, 270 MHz)

δ: 0.99(3H, t, J=7.4 Hz), 1.3-1.8(10H, m), 2.15-2.35(2H, m), 3.3-3.6(6H, m), 4.1-4.25(2H, m), 7.25-7.5(5H, m), 7.91(1H, s)

IR (neat): νCO 1710, 1650 cm⁻¹

EXAMPLE 34

Propyl (E)-2-(4-methylbenzylidene)-3-(cis-3a,4,7,7a-tetrahydro-2-isoindolinylcarbonyl)propionate To a solution of (E)-2-(4-methylbenzylidene)-3-(cis-3a,4,7,7a-tetrahydro-2-isoindolinylcarbonyl)-propionic acid (310 mg) in N,N-dimethylformamide (20 ml) were added triethylamine (105 mg) and propyl bromide (125 mg) and the mixture was stirred at room temperature for 15 hours. To the reaction mixture was added water and the mixture was extracted with ethyl acetate. The organic layer was washed successively with 1N hydrochloric acid, saturated sodium bicarbonate solution, and brine and dried over MgSO₄. After the solvent was evaporated under reduced pressure, the residue was purified by column chromatography on silica gel eluting with hexane/ethyl acetate (4/1) to give 165 mg of propyl (E)-2-(4-methylbenzylidene)-3-(cis-3a,4,7,7a-tetrahydro-2-isoindolinyl)propionate as a colorless viscous oil.

NMR (CDCl₃, 270 MHz)

δ: 0.95-1.05(3H, m), 1.65-1.8(2H, m), 1.85-2.05 (2H, m), 2.15-2.55(7H, m), 3.25-3.7(6H, m), 4.05-4.25(2H, m), 5.6-5.75(2H, m), 7.1-7.4(4H, m), 7.89(1H, s)

IR (neat): νCO 1710, 1650 cm⁻¹

EXAMPLE 35

In a similar manner to that described in example 34, the following compound was prepared from (E)-2-(2-chlorobenzylidene)-3-(cis-hexahydro-2-isoindolinylcarbonyl)propionic acid instead of (E)-2-(4-methylbenzylidene)-3-(cis-3a,4,7,7a-tetrahydro-2-isoindolinylcarbonyl)propionic acid.

Propyl (E)-2-(2-chlorobenzylidene)-3-(cis-hexahydro-2-isoindolinylcarbonyl)propionate Colorless viscous oil
NMR (CDCl$_3$, 270 MHz)
δ: 1.00(3H, t, J=7.4 Hz), 1.25-1.85(10H, m), 2.1-2.4(2H, m), 3.25-3.6(6H, m), 4.18(2H, t, J=6.4 Hz), 7.2-7.75(4H, m), 7.96(1H, s)
IR (neat): νCO 1720, 1650 cm$^{-1}$

EXAMPLE 36

2-Benzyl-3-(trans-decahydro-2-isoquinolylcarbonyl)propionic acid

To a suspension of (E)-2-benzylidene-3-(trans-decahydro-2-isoquinolylcarbonyl)propionic acid (200 mg) in ethanol (2 ml) was added 10% Pd-C (20 mg) and the mixture was hydrogenated at room temperature and atmospheric pressure for 16 hours. After the catalyst was filtered off, the solvent was evaporated under reduced pressure to give 188 mg of 2-benzyl-3-(trans-decahydro-2-isoquinolylcarbonyl)propionic acid as a colorless viscous oil.

NMR (DMSO-d$_6$, 270 MHz)
δ: 0.8-1.3(7H, m), 1.4-1.8(5H, m), 2.0-3.05 (7H, m), 3.55-3.85(1H, m), 4.2-4.5(1H, m), 7.1-7.35(5H, m)
IR (neat): νCO 1735, 1645, 1605 cm$^{-1}$

EXAMPLE 37

In a similar manner to that described in example 36, the following compound was prepared from (E)-2-benzylidene-3-(trans-hexahydro-2-isoindolinylcarbonyl)propionic acid instead of (E)-2-benzylidene-3-(trans-decahydro-2-isoquinolylcarbonyl)propionic acid.

2-Benzyl-3-(trans-hexahydro-2-isoindolinylcarbonyl)propionic acid

Melting point: 151°-156° C. (crystallized from diethyl ether)
NMR (CDCl$_3$, 270 MHz)
δ: 0.95-1.55(6H, m), 1.7-2.0(4H, m), 2.35-2.9(5H, m), 7.35(5H, m)
IR (KBr): νCO 1730, 1595 cm$^{-1}$

EXAMPLE 38

In a similar manner to that described in example 36, the following compound was prepared from (E)-2-benzylidene-3-(trans-hexahydro-1-indolinylcarbonyl)propionic acid instead of (E)-2-benzylidene-3-(trans-decahydro-2-isoquinolylcarbonyl)propionic acid. 2-Benzyl-3-(trans-hexahydro-1-indolinylcarbonyl)propionic acid.

Colorless viscous oil
NMR (CDCl$_3$, 270 MHz)
δ: 0.85-2.3(11H, m), 2.35-2.85(3H, m), 2.95-3.55(4H, m), 3.95-4.1(1H, m), 7.1-7.4(5H, m)
IR (neat): νCO 1730, 1605 cm$^{-1}$

EXAMPLE 39

In a similar manner to that described in example 36, the following compound was prepared from (E)-2-benzylidene-3-(cis-hexahydro-2-isoindolinylcarbonyl)propionic acid instead of (E)-2-benzylidene-3-(trans-decahydro-2-isoquinolylcarbonyl)propionic acid.

2-Benzyl-3-(cis-hexahydro-2-isoindolinylcarbonyl)propionic acid

Melting point: 124°-125° C. (recrystallized from diethyl ether)
NMR (CDCl$_3$, 270 MHz)
δ: 1.15-1.7(8H, m), 2.05-2.3(2H, m), 2.35-2.55(2H, m), 2.65-3.5(7H, m), 7.1-7.4(5H, m)
IR (KBr): νCO 1730, 1610 cm$^{-1}$

EXAMPLE 40

Benzyl (S)-2-benzyl-3-(cis-hexahydro-2-isoindolinylcarbonyl)propionate

To a solution of (S)-3-benzyloxycarbonyl-4-phenylbutyric acid (671 mg) in anhydrous tetrahydrofuran (15 ml) were added N-methylmorpholine (0.5 ml) and isobutyl chloroformate (0.38 ml) with stirring at −20° C. for 20 minutes. To the mixture was added a solution of cis-hexahydroisoindoline (313 mg) in anhydrous tetrahydrofuran (5 ml) with stirring at −10 - −20° C. After 1 hour, the deposit was filtered off and the solvent was evaporated under reduced pressure. The residue was dissolved in ethyl acetate and washed successively with 0.5N hydrochloric acid, saturated sodium bicarbonate solution, and brine and dried over MgSO$_4$. After the solvent was evaporated under reduced pressure, the residue was recrystallized from dichloromethane-hexane to give 772 mg of benzyl (S)-2-benzyl-3-(cis-hexahydro-2-isoindolinylcarbonyl)propionate.

Melting point: 107°-108° C.
NMR (CDCl$_3$, 400 MHz)
δ: 1.3-1.65(8H, m), 2.1-2.35(3H, m), 2.55-2.7(1H, m), 2.8-2.9(1H, m), 3.0-3.45(6H, m), 5.0-5.2 (2H, m), 7.1-7.4(10H, m)
IR (KBr): νCO 1735, 1630 cm$^{-1}$
$[α]_D^{17.5} = -5.5°$ (c=1.0, CHCl$_3$)

EXAMPLE 41

(S)-2-Benzyl-3-(cis-hexahydro-2-isoindolinylcarbonyl)propionic acid

To a solution of benzyl (S)-2-benzyl-3-(cis-hexahydro-2-isoindolinylcarbonyl)propionate (400 mg) in ethyl acetate (3 ml) was added 10% Pd-C (60 mg) and the mixture was hydrogenolyzed at room temperature and atmospheric pressure for 16 hours. After the catalyst was filtered off, the solvent was evaporated under reduced pressure to give 227 mg of (S)-2-benzyl-3-(cis-hexahydro-2-isoindolinylcarbonyl)propionic acid as a colorless viscous oil.

NMR (CDCl$_3$, 270 MHz)
δ: 1.15-1.7(8H, m), 2.05-2.3(2H, m), 2.35-2.55(2H, m), 2.65-3.5(7H, m), 7.1-7.4(5H, m)
IR (neat): νCO 1735, 1605 cm$^{-1}$
$[α]_D^{17.5} = -3.5°$ (c=1.0, MeOH)

EXAMPLE 42

In a similar manner to that described in example 40, the following compound was prepared from (R)-3-benzyloxycarbonyl-4-phenylbutyric acid instead of (S)-3-benzyloxycarbonyl-4-phenylbutyric acid.

Benzyl (R)-2-benzyl-3-(cis-hexahydro-2-isoindolinylcarbonyl)-propionate

Melting point: 107°–108° C. (recrystallized from dichloromethane-hexane)
NMR (CDCl$_3$, 400 MHz)
δ: 1.3–1.65(8H, m), 2.1–2.35(3H, m), 2.55–2.7(1H, m), 2.8–2.9(1H, m), 3.0–3.45(6H, m), 5.0–5.2 (2H, m), 7.1–7.4(10H, m)
IR (KBr): νCO 1735, 1630 cm$^{-1}$
[α]$_D^{17.5}$ = 5.2° (c = 1.0, CHCl$_3$)

EXAMPLE 43

In a similar manner to that described in example 41, the following compound was prepared from benzyl (R)-2-benzyl-3-(cis-hexahydro-2-isoindolinylcarbonyl)-propionate instead of benzyl (S)-2-benzyl-3-(cis-hexahydro-2-isoindolinylcarbonyl)propionate.

(R)-2-Benzyl-3-(cis-hexahydro-2-isoindolinylcarbonyl)-propionic acid

Colorless viscous oil
NMR (CDCl$_3$, 270 MHz)
δ: 1.15–1.7(8H, m), 2.05–2.3(2H, m), 2.35–2.55(2H, m), 2.65–3.5(7H, m), 7.1–7.4(5H, m)
IR (neat): νCO 1735, 1605 cm$^{-1}$
[α]$_D^{17.5}$ = 2.9° (c = 1.0, MeOH)

EXAMPLE 44

In a similar manner to that described in example 40, the following compound was prepared from 4-phenyl-3-propoxycarbonylbutyric acid and cis-a,4,7,7a-tetrahydroisoindoline instead of (S)-3-benzyloxycarbony-4-phenylbutyric acid and cis-hexahydroisoindoline.

Propyl 2-benzyl-3-(cis-3a,4,7,7a-tetrahydro-2-isoindolinylcarbonyl)propionate

Colorless viscous oil
NMR (CDCl$_3$, 270 MHz)
δ: 0.8–0.9(3H, m), 1.5–1.7(2H, m), 1.75–1.95(2H, m), 2.15–2.45(5H, m), 2.55–2.7(1H, m), 2.75–2.9(1H, m), 2.95–3.1(1H, m), 3.15–3.55(5H, m), 4.0(2H, t, J=6.6 Hz), 5.55–5.75(2H, m), 7.1–7.35(5H, m)
IR (neat): νCO 1730, 1650 cm$^{-1}$

EXAMPLE 45

2-Benzyl-3-(cis-3a,4,7,7a-tetrahydro-2-isoindolinylcarbonyl)propionic acid

To a solution of propyl 2-benzyl-3-(cis-3a,4,7,7a-tetrahydro-2-isoindolinylcarbonyl)propionate (198 mg) in ethanol (2 ml) was added 1N sodium hydroxide solution (668 μl) and the mixture was stirred at room temperature for 16 hours. After the solvent was evaporated under reduced pressure, the residue was dissolved in water and extracted with ethyl acetate. The aqueous layer was acidified with hydrochloric acid and extracted with ethyl acetate. The organic layer was washed with brine and dried over MgSO$_4$. After the solvent was evaporated under reduced pressure, the residue was crystallized from diethyl ether to give 120 mg of 2-benzyl-3-(cis-3a,4,7,7a-tetrahydro-2-isoindolinylcarbonyl)propionic acid.
Melting point: 128°–132° C.
NMR (CDCl$_3$, 270 MHz)
δ: 1.7–1.9(2H, m), 2.15–2.55(6H, m), 2.7–3.0(2H, m), 3.05–3.6(5H, m), 5.55–5.75(2H, m), 7.1–7.35(5H, m)
IR (KBr): νCO 1730, 1615 cm$^{-1}$

EXAMPLE 46

2-(4-Methylbenzyl)-3-(cis-3a,4,7,7a-tetrahydro-2-isoindolinylcarbonyl)propionic acid To a solution of di(4-nitrophenyl) 2-(4-methylbenzyl)succinate (2.4 g) in N,N-dimethylformamide (30 ml) was added a solution of cis-3a,4,7,7a-tetrahydroisoindoline (0.62 g) in N,N-dimethylformamide (10 ml) with stirring at 0° C. After stirring at 0° C. for 3 hours, water was added to the reaction mixture and extracted with ethyl acetate. The organic layer was washed successively with three 1N sodium hydroxide solutions, 1N-hydrochloric acid, and brine and dried over MgSO$_4$. After the solvent was evaporated under reduced pressure, the residue was recrystallized from hexane-ethyl acetate (4:1) to give 1.7 g of 4-nitrophenyl 2-(4-methylbenzyl)-3-(cis-3a,4,7,7a-tetrahydro-2-isoindolinylcarbonyl)propionate.

To a suspension of 4-nitrophenyl 2-(4-methylbenzyl)-3-(cis-3a,4,7,7a-tetrahydro-2-isoindolinylcarbonyl)propionate (1.7 g) in methanol (10 ml) was added 1N sodium hydroxide solution (8.0 ml) and the mixture was stirred at room temperature for 15 hours. The reaction mixture was acidified with 1N hydrochloric acid under ice-cooling and extracted with ethyl acetate. The organic layer was washed with brine and dried over MgSO$_4$. After the solvent was evaporated under reduced pressure, the residue was purified by column chromatography on silica gel eluting with hexane/ethyl acetate (2/1) to give 0.4 g of 2-(4-methylbenzyl)-3-(cis-3a,4,7,7a-tetrahydro-2-isoindolinylcarbonyl)propionic acid as a colorless crystal.
Melting point: 140°–141° C.
NMR (CDCl$_3$, 270 MHz)
δ: 1.7–1.95(2H, m), 2.1–2.6(9H, m), 2.65–2.95(2H, m), 3.05–3.4(4H, m), 3.45–3.6(1H, m), 5.55–5.75(2H, m), 7.0–7.2(4H, m)
IR (KBr): νCO 1730, 1610 cm$^{-1}$

EXAMPLE 47

3-(cis-Hexahydro-2-isoindolinylcarbonyl)-2-(4-methylbenzyl)propionic acid

To a suspension of (E)-3-(cis-hexahydro-2-isoindolinylcarbonyl)-2-(4-methylbenzylidene)propionic acid (250 mg) in ethanol (10 ml) was added 10% Pd-C (20 mg) and the mixture was hydrogenated at room temperature and atmospheric pressure for 16 hours. After the catalyst was filtered off, the solvent was evaporated under reduced pressure and the residue was crystallized from diethyl ether to give 220 mg of 3-(cis-hexahydro-2-isoindolinylcarbonyl)-2-(4-methylbenzyl)propionic acid.
Melting point: 133°–134° C.
NMR (CDCl$_3$, 270 MHz)
δ: 1.2–1.7(8H, m), 2.05–2.3(2H, m), 2.32(3H, s), 2.45–2.55(2H, m), 2.65–2.8(1H, m), 2.85–3.5(6H, m), 7.0–7.2(4H, m)
IR (KBr): νCO 1730, 1600 cm$^{-1}$

EXAMPLE 48

In a similar manner to that described in example 47, the following compound was prepared from (E)-3-(cis-hexahydro-2-isoindolinylcarbonyl)-2-(2-methylbenzylidene)propionic acid instead of (E)-3-(cis-hexahydro-2-isoindolinylcarbonyl)-2-(4-methylbenzylidene)-propionic acid.

3-(cis-Hexahydro-2-isoindolinylcarbonyl)-2-(2-methylbenzyl)propionic acid

Melting point: 109°–110° C.
NMR (DMSO-d$_6$, 270 MHz)
δ: 1.15–1.65(8H, m), 2.0–2.35(5H, m), 2.5–3.0(3H, m), 3.05–3.55(6H, m), 7.0–7.2(4H, m), 11.80 (1H, bs)
IR (KBr): νCO 1730, 1630 cm$^{-1}$

EXAMPLE 49

In a similar manner to that described in example 47, the following compound was prepared from (E)-2-(3-methylbenzylidene)-3-(cis-3a,4,7,7a-tetrahydro-2-isoindolinylcarbonyl)propionic acid instead of (E)-3-(cis-hexahydro-2-isoindolinylcarbonyl)-2-(4-methylbenzylidene)propionic acid.

3-(cis-Hexahydro-2-isoindolinylcarbonyl)-2-(3-methylbenzyl)propionic acid

Melting point: 106°–107° C.
NMR (CDCl$_3$, 270 MHz)
δ: 1.2–1.7(8H, m), 2.1–2.3(2H, m), 2.33 (3H, s), 2.35–2.6(2H, m), 2.65–3.15(4H, m), 3.2–3.55(3H, m), 6.9–7.25(4H, m)
IR (KBr): νCO 1750, 1590 cm$^{-1}$

EXAMPLE 50

In a similar manner to that described in example 47, the following compound was prepared from (E)-3-(cis-hexahydro-2-isoindolinylcarbonyl)-2-(2-isopropylbenzylidene)propionic acid instead of (E)-3-(cis-hexahydro-2-isoindolinylcarbonyl)-2-(4-methylbenzylidene)propionic acid.

3-(cis-Hexahydro-2-isoindolinylcarbonyl)-2-(2-isopropylbenzyl)propionic acid

Colorless amorphous solid
NMR (CDCl$_3$, 270 MHz)
δ: 1.1–1.7(14H, m), 2.05–2.3(2H, m), 2.35–2.6(2H, m), 2.7–3.5(8H, m), 7.0–7.35(4H, m)
IR (KBr): νCO 1735, 1650, 1610 cm$^{-1}$

EXAMPLE 51

In a similar manner to that described in example 47, the following compound was prepared from (E)-2-(4-methoxybenzylidene)-3-(cis-3a,4,7,7a-tetrahydro-2-isoindolinylcarbonyl)propionic acid instead of (E)-3-(cis-hexahydro-2-isoindolinylcarbonyl)-2-(4-methylbenzylidene)propionic acid.

3-(cis-Hexahydro-2-isoindolinylcarbonyl)-2-(4-methoxybenzyl)propionic acid

Melting point: 153°–154° C.
NMR (CDCl$_3$, 270 MHz)
δ: 1.25–1.7(8H, m), 2.1–2.3(2H, m), 2.4–2.55(2H, m), 2.65–2.8(1H, m), 2.85–3.55(6H, m), 3.79 (3H, s), 6.8–7.15(4H, m)
IR (KBr): νCO 1730, 1610 cm$^{-1}$

EXAMPLE 52

In a similar manner to that described in example 47, the following compound was prepared from (E)-3-(cis-hexahydro-2-isoindolinylcarbonyl)-2-(2-methoxybenzylidene)propionic acid instead of (E)-3-(cis-hexahydro-2-isoindolinylcarbonyl)-2-(4-methylbenzylidene)propionic acid.

3-(cis-Hexahydro-2-isoindolinylcarbonyl)-2-(2-methoxybenzyl)propionic acid

Colorless amorphous solid
NMR (CDCl$_3$, 270 MHz)
δ: 1.2–1.7(8H, m), 2.1–2.25(2H, m), 2.35–2.6(2H, m), 2.7–3.5(7H, m), 3.81(3H, s), 6.8–7.3(4H, m)
IR (KBr): νCO 1730, 1650, 1600 cm$^{-1}$

EXAMPLE 53

In a similar manner to that described in example 47, the following compound was prepared from (E)-2-(2-ethoxybenzylidene)-3-(cis-hexahydro-2-isoindolinylcarbonyl)propionic acid instead of (E)-3-(cis-hexahydro-2-isoindolinylcarbonyl)-2-(4-methylbenzylidene)propionic acid.

2-(2-Ethoxybenzyl)-3-(cis-hexahydro-2-isoindolinylcarbonyl)propionic acid

Colorless amorphous solid
NMR (CDCl$_3$, 400 MHz)
δ: 1.2–1.65(11H, m), 2.1–2.25(2H, m), 2.4–2.6(2H, m), 2.7–3.5(7H, m), 4.0–4.1(2H, m), 6.8–7.25 (4H, m)
IR (KBr): νCO 1735, 1640, 1600 cm$^{-1}$

EXAMPLE 54

In a similar manner to that described in example 47, the following compound was prepared from (E)-3-(cis-hexahydro-2-isoindolinylcarbonyl)-2-(2-propoxybenzylidene)propionic acid instead of (E)-3-(cis-hexahydro-2-isoindolinylcarbonyl)-2-(4-methylbenzylidene)propionic acid.

3-(cis-Hexahydro-2-isoindolinylcarbonyl)-2-(2-propoxybenzyl)propionic acid

Colorless amorphous solid
NMR (CDCl$_3$, 400 MHz)
δ: 1.0–1.1(3H, m), 1.15–1.65(8H, m), 1.75–1.9(2H, m), 2.05–2.25(2H, m), 2.4–2.55(2H, m), 2.7–3.5(7H, m), 3.85–4.0(2H, m), 6.75–7.25(4H, m)
IR (KBr): νCO 1730, 1650, 1600 cm$^{-1}$

EXAMPLE 55

In a similar manner to that described in example 47, the following compound was prepared from (Z)-2-(2,6-dimethylbenzylidene)-3-(cis-hexahydro-2-isoindolinylcarbonyl)propionic acid instead of (E)-3-(cis-hexahydro-2-isoindolinylcarbonyl)-2-(4-methylbenzylidene)propionic acid.

2-(2,6-Dimethylbenzyl)-3-(cis-hexahydro-2-isoindolinylcarbonyl)propionic acid

Colorless amorphous solid
NMR (CDCl$_3$, 270 MHz)
δ: 1.2–1.65(8H, m), 2.05–2.45(9H, m), 2.5–2.65(1H, m), 2.75–3.5(7H, m), 6.95–7.1(3H, m)
IR (KBr): νCO 1730, 1650, 1610 cm$^{-1}$

EXAMPLE 56

In a similar manner to that described in example 47, the following compound was prepared from (E)-2-(2,6-dimethoxybenzylidene)-3-(cis-hexahydro-2-isoindolinylcarbonyl)propionic acid instead of (E)-3-(cis-hexahydro-2-isoindolinylcarbonyl)-2-(4-methylbenzylidenecarbonyl)propionic acid.

2-(2,6-Dimethoxybenzyl)-3-(cis-hexahydro-2-isoindolinylcarbonyl)propionic acid

Colorless amorphous solid
NMR (CDCl$_3$, 270 MHz)
δ: 1.25–1.65(8H, m), 2.1–2.25(2H, m), 2.45–2.55(2H, m), 2.75–3.55(7H, m), 3.80(6H, s), 6.5–6.6(2H, m), 7.1–7.25(1H, m)
IR (KBr): νCO 1740, 1710, 1650, 1600 cm$^{-1}$

EXAMPLE 57

3-(cis-Hexahydro-2-isoindolinylcarbonyl)-2-(2-thienyl)propionic acid

To a suspension of (E)-3-(cis-hexahydro-2-isoindolinylcarbonyl)-2-(2-thenylidene)propionic acid (150 mg) in ethanol (20 ml) was added 10% Pd-C (70 mg) and the mixture was hydrogenated at room temperature and atmospheric pressure for 16 hours. After the catalyst was filtered off, the solvent was evaporated under reduced pressure. The residue was purified by thin layer chromatography (mobile phase: dichloromethane/methanol=15/1) to give 30 mg of 3-(cis-hexahydro-2-isoindolinylcarbonyl)-2-(2-thenyl)propionic acid as a pale yellow viscous oil.
NMR (CDCl$_3$, 270 MHz)
δ: 1.15–1.75(8H, m), 2.1–2.7(4H, m), 2.95–3.55 (7H, m), 6.84(1H, d, J=3.3 Hz), 6.9–7.0(1H, m), 7.15–7.2(1H, m)
IR (neat): νCO 1750, 1630, 1595 cm$^{-1}$

EXAMPLE 58

In a similar manner to that described in example 47, the following compound was prepared from (E)-2-cyclohexylmethylene-3-(cis-hexahydro-2-isoindolinylcarbonyl)propionic acid instead of (E)-3-(cis-hexahydro-2-isoindolinylcarbonyl)-2-(4-methylbenzylidene)propionic acid.

2-Cyclohexylmethyl-3-(cis-hexahydro-2-isoindolinylcarbonyl)propionic acid

Melting point: 116°–117° C.
NMR (CDCl$_3$, 270 MHz)
δ: 0.75–1.9(21H, m), 2.15–2.7(4H, m), 2.9–3.1(1H, m), 3.15–3.55(4H, m), 12.3(1H, br)
IR (KBr): νCO 1735, 1595 cm$^{-1}$

EXAMPLE 59

Methyl 2-benzyl-3-(cis-hexahydro-2-isoindolinylcarbonyl)propionate

To 2-benzyl-3-(cis-hexahydro-2-isoindolinylcarbonyl)propionic acid (100 mg) was added a 3% solution of hydrogen chloride in methanol (2 ml) and the mixture was stirred at room temperature for 16 hours. The solvent was evaporated under reduced pressure and the residue was dissolved in dichloromethane. The solution was washed successively with saturated sodium bicarbonate solution and brine, treated with activated charcoal, and dried over MgSO$_4$. The solvent was evaporated under reduced pressure to give 91 mg of methyl 2-benzyl-3-(cis-hexahydro-2-isoindolinylcarbonyl)propionate as a colorless viscous oil.
NMR (CDCl$_3$, 270 MHz)
δ: 1.25–1.65(8H, m), 2.05–2.35(3H, m), 2.55–2.7(1H, m), 2.75–2.9(1H, m), 2.95–3.5(6H, m), 3.65(3H, s), 7.1–7.35(5H, m)
IR (neat): νCO 1730, 1650 cm$^{-1}$

EXAMPLE 60

Methyl 3-(cis-hexahydro-2-isoindolinylcarbonyl)-2-(4-methylbenzyl)propionate

To a suspension of 3-(cis-hexahydro-2-isoindolinylcarbonyl)-2-(4-methylbenzyl)propionic acid (100 mg) in diethyl ether (10 ml) was added a solution of diazomethane in diethyl ether (10 ml) with stirring at 0° C. After the mixture was stirred at room temperature for 1 hour, excess diazomethane was decomposed with acetic acid. The reaction mixture was washed successively with saturated sodium bicarbonate solution and brine and dried over MgSO$_4$. After the solvent was evaporated under reduced pressure, the residue was purified by column chromatography on silica gel eluting with hexane/ethyl acetate (4/1) to give 60 mg of methyl 3-(cis-hexahydro-2-isoindolinylcarbonyl)-2-(4-methylbenzyl)propionate as a colorless viscous oil.
NMR (CDCl$_3$, 270 MHz)
δ: 1.25–1.65(8H, m), 2.05–2.3(3H, m), 2.31(3H, s), 2.5–2.85(2H, m), 2.9–3.05(1H, m), 3.1–3.5(5H, m), 3.66(3H, s), 7.0–7.15(4H, m)
IR (neat): νCO 1740, 1735, 1650, 1645 cm$^{-1}$

EXAMPLE 61

In a similar manner to that described in example 60, the following compound was prepared from 3-(cis-hexahydro-2-isoindolinylcarbonyl)-2-(2-methylbenzyl)propionic acid instead of 3-(cis-hexahydro-2-isoindolinylcarbonyl)-2-(4-methylbenzyl)propionic acid.

Methyl 3-(cis-hexahydro-2-isoindolinylcarbonyl)2-(2-methylbenzyl)propionate

Colorless viscous oil
NMR (CDCl$_3$, 270 MHz)
δ: 1.25–1.7(8H, m), 2.1–2.35(3H, m), 2.35(3H, s), 2.6–2.85(2H, m), 2.95–3.5(6H, m), 3.64(3H, s), 7.05–7.25(4H, m)
IR (neat): νCO 1750, 1650 cm$^{-1}$

EXAMPLE 62

In a similar manner to that described in example 60, the following compound was prepared from 3-(cis-hexahydro-2-isoindolinylcarbonyl)-2-(3-methylbenzyl)propionic acid instead of 3-(cis-hexahydro-2-isoindolinylcarbonyl)-2-(4-methylbenzyl)propionic acid.

Methyl 3-(cis-hexahydro-2-isoindolinylcarbonyl)-2-(3-methylbenzyl)propionate

Colorless viscous oil
NMR (CDCl$_3$, 270 MHz)
δ: 1.25–1.7(8H, m), 2.05–2.3(3H, m), 2.32(3H, s), 2.55–2.85(2H, m), 2.95–3.05(1H, m), 3.1–3.5(5H, m). 3.66(3H, s). 6.9–7.25(4H, m)
IR (neat): νCO 1750, 1650 cm$^{-1}$

EXAMPLE 63

Propyl 2-benzyl-3-(cis-hexahydro-2-isoindolinylcarbonyl)propionate

To 2-benzyl-3-(cis-hexahydro-2-isoindolinylcarbonyl)propionic acid (100 mg) were added propanol (2 ml) and boron trifluoride diethyl ether complex (12 μl) with stirring. After the mixture was stirred at room temperature for 24 hours, the solvent was evaporated under reduced pressure. The residue was dissolved in dichloromethane, washed succecively with saturated sodium bicarbonate solution and brine, and dried over MgSO$_4$. The solvent was evaporated under reduced pressure to give 106 mg of propyl 2-benzyl-3-(cis-hexahydro-2-isoindolinylcarbonyl)propionate as a colorless viscous oil.

NMR (CDCl$_3$, 270 MHz)

δ: 0.8–0.9(3H, m), 1.25–1.7(10H, m), 2.1–2.35(3H, m), 2.55–2.7(1H, m), 2.75–2.9(1H, m), 2.95–3.5(6H, m), 4.0(2H, t, J=6.6 Hz), 7.15–7.35(5H, m)

IR (neat): νCO 1730, 1650 cm$^{-1}$

EXAMPLE 64

Propyl 3-(cis-hexahydro-2-isoindolinylcarbonyl)-2-(4-methylbenzyl)propionate

To a solution of 3-(cis-hexahydro-2-isoindolinylcarbonyl)-2-(4-methylbenzyl)propionic acid (100 mg) in N,N-dimethylformamide (2 ml) were added triethylamine (50 mg) and propyl bromide (100 mg) and the mixture was stirred at room temperature for 15 hours. To the reaction mixture was added water (10 ml) and the mixture was extracted with ethyl acetate. The organic layer was washed succesively with 1N hydrochloric acid, saturated sodium bicarbonate solution, and brine and dried over MgSO$_4$. After the solvent was evaporated under reduced pressure, the residue was purified by column chromatography on silica gel eluting with hexane/ethyl acetate (4/1) to give 30 mg of propyl 3-(cis-hexahydro-2-isoindolinylcarbonyl)-2-(4-methylbenzyl)propionate as a colorless viscous oil.

NMR (CDCl$_3$, 270 MHz)

δ: 0.8–0.95(3H, m), 1.25–1.75(10H, m), 2.05–2.3 (3H, m), 2.31(3H, s), 2.5–2.85(2H, m), 2.95–3.05(1H, m), 3.1–3.45(5H, m), 3.95–4.05(2H, m), 7.0–7.15(4H, m)

IR (neat): νCO 1735, 1650 cm$^{-1}$

EXAMPLE 65

In a similar manner to that described in example 63, the following compound was prepared from 3-(cis-hexahydro-2-isoindolinylcarbonyl)-2-(4-methoxybenzyl)-propionic acid instead of 2-benzyl-3-(cis-hexahydro-2-isoindolinylcarbonyl)propionic acid.

Propyl 3-(cis-hexahydro-2-isoindolinylcarbonyl)-2-(4-methoxybenzyl)propionate

Colorless viscous oil

NMR (CDCl$_3$, 270 MHz)

δ: 0.8–0.95(3H, m), 1.25–1.8(10H, m), 2.05–2.35 (3H, m), 2.55–2.85(2H, m), 2.9–3.05(1H, m), 3.1–3.5(5H, m), 3.78(3H, s), 4.00(2H, t, J=6.6 Hz), 6.75–7.15(4H, m)

IR (neat): νCO 1730, 1650, 1610 cm$^{-1}$

EXAMPLE 66

Sodium (S)-2-benzyl-3-(cis-hexahydro-2-isoindolinylcarbonyl)-propionate monohydrate To a solution of (S)-2-benzyl-3-(cis-hexahydro-2-isoindolinylcarbonyl)propionic acid (1.38 g) in ethanol (5 ml) was added 2N sodium hydroxide solution (2.19 ml). After the solvent was evaporated under reduced pressure, the residue was crystallized from ethyl acetate to give 1.44 g of sodium (S)-2-benzyl-3-(cis-hexahydro-2-isoindolinylcarbonyl)propionate monohydrate.

Melting point: 172°–174° C.

NMR (DMSO-d$_6$, 270 MHz)

δ: 1.15–1.55(8H, m), 1.85–3.5(13H, m), 7.05–7.3 (5H, m)

IR (KBr): νCO 1630 cm$^{-1}$

[α]$_D^{17.5}$=−10.3° (c=1.1, H$_2$O)

EXAMPLE 67

In a similar manner to that described in example 66, the following compound was prepared from 1N potassium hydroxide solution instead of 2N sodium hydroxide solution.

Potassium (S)-2-benzyl-3-(cis-hexahydro-2-isoindolinylcarbonyl)-propionate monohydrate Melting point: 198°–200° C.

NMR (DMSO-d$_6$, 400 MHz)

δ: 1.2–1.55(8H, m), 1.85–2.2(3H, m), 2.4–2.65(3H, m), 2.85–3.55(5H, m), 3.4(2H, bs), 7.05–7.55(5H, m)

IR (KBr): νCO 1630 cm$^{-1}$

[α] 17 5 D=−8.6° (c=1.1, H$_2$O)

EXAMPLE 68

Calcium bis(S)-2-benzyl-3-(cis-hexahydro-2-isoindolinylcarbonyl)propionate dihydrate (S)-2-Benzyl-3-(cis-hexahydro-2-isoindolinylcarbonyl)propionic acid (133 mg) was dissolved in water (4 ml) by addition of 25% ammonia solution (0.2 ml). To the mixture was added a solution of calcium chloride (111 mg) in water (2 ml) and the precipitated crystals were collected by filtration. The crystals were dried and recrystallized from diisopropyl ether to give 117 mg of calcium bis(S)-2-benzyl-3-(cis-hexahydro-2-isoindolinylcarbonyl)propionate dihydrate.

Melting point: 179°–185° C.

NMR (DMSO-d$_6$, 270 MHz)

δ: 1.2–1.65(16H, m), 2.0–2.3(6H, m), 2.55–3.6 (20H, m), 7.15–7.4(10H, m)

IR (KBr): νCO 1660, 1625 cm$^{-1}$

[α]$_D^{17.5}$=5.7° (c=1.0, MeOH)

EXAMPLE 69

L-Arginine salt of (S)-2-benzyl-3-(cis-hexahydro-2-isoindolinylcarbonyl)-propionic acid To a solution of (S)-2-benzyl-3-(cis-hexahydro-2-isoindolinylcarbonyl)propionic acid (86.4 mg) in ethanol (5 ml) was added a solution of L-arginine (47.7 mg) in water (3 ml) and the mixture was stirred at room temperature for 1 hour. After the solvent was evaporated under reduced pressure, the residue was crystallized from ethanol-diethyl ether to give 130 mg of L-arginine salt of (S)-2-benzyl-3-(cis-hexahydro-2-isoindolinylcarbonyl)propionic acid.

Melting point: 131°–137° C.

NMR (DMSO-d$_6$, 270 MHz)

δ: 1.15–1.8(11H, m), 1.9–2.25(3H, m), 2.35–3.4 (12H, m), 7.1–7.3(5H, m), 7.5–8.5(4H, m)

IR (KBr): νCO 1630 cm$^{-1}$

[α]$_D^{17.5}$=4.0° (c=1.0, MeOH)

EXAMPLE 70

In a similar manner to that described in example 69, the following compound was prepared from D-phenylalaninol instead of L-arginine.

D-Phenylalaninol salt of
(S)-2-benzyl-3-(cis-hexahydro-2-isoindolinylcarbonyl)-propionic acid Melting point: 131°-134° C. (crystallized from ethyl acetate)
NMR (CDCl$_3$, 270 MHz)
δ: 1.2–1.6(8H, m), 1.95–2.3(3H, m), 2.45–3.4(11H, m), 3.45–3.6(1H, m), 3.65–3.8(1H, m), 6.85(4H, bs), 7.1–7.4(10H, m)
IR (KBr): νCO 1635 cm$^{-1}$
[α]$_D^{17.5}$ = 5.8° (c=1.0, CHCl$_3$)

TEST EXAMPLE 1

Islets were prepared from mouse pancreas by collagenase digestion methods. (Transplantation, Vol. 43, pages 725–730, (1987))

Group of 3 freshly isolated islets were preincubated at 37° C. in 0.6 ml Krebs-Ringer bicarbonate buffer (KRB) containing 5.5 mM glucose, 0.2% bovine serum albumin and 5 mM HEPES (4-(2-hydroxyethyl)-1-piperazineethanesulfonic acid).

Islets were preincubated 1 hour under 95% O$_2$: 5% CO$_2$ and then preincubation buffer was replaced with 0.6 ml KRB incubation medium containing test compound or vehicle. After 90 minutes at 37° C., insulin content released in incubation medium was determined with RIA kit. Activities were shown by symbols which mean the compound concentration required for 100% increase in insuline secretion over vehicle alone in a range of <0.1 μM (++++), 0.1–1 μM (+++), 1–10 μM (++) and 10–100 +M (+).

| Example No. | Activity of the title compound | Example No. | Activity of the title compound |
|---|---|---|---|
| 1 | ++++ | 36 | ++ |
| 2 | ++++ | 37 | +++ |
| 3 | +++ | 38 | +++ |
| 4 | ++ | 39 | ++++ |
| 5 | +++ | 41 | ++++ |
| 6 | +++ | 43 | ++++ |
| 7 | ++ | 45 | +++ |
| 8 | ++ | 46 | + |
| 9 | ++ | 47 | +++ |
| 10 | +++ | 48 | +++ |
| 11 | +++ | 49 | ++ |
| 12 | +++ | 50 | ++ |
| 13 | ++ | 51 | ++ |
| 14 | +++ | 52 | +++ |
| 15 | + | 53 | ++ |
| 16 | +++ | 54 | +++ |
| 17 | ++ | 55 | ++++ |
| 19 | +++ | 56 | ++ |
| 21 | +++ | 57 | +++ |
| 22 | ++++ | 58 | +++ |
| 23 | + | 66 | ++++ |
| 24 | ++++ | 67 | ++++ |
| 25 | ++++ | 69 | ++++ |

TEST EXAMPLE 2

Test formulations were prepared by suspending the test compound in a vehicle consisting of 0.5% (w/v) carboxymethylcellulose sodium in water to provide dose lever of 0/1-3 mg/kg. Each test compound or vehicle was administered to 5 ICR mice or SD rats by gavage. Evaluations of the blood glucose level were recorded at 1 hour for mice and 30 minutes for rats following administration.

| Example No. | Mouse Dose (mg/kg) of the title compound | Blood Glucose (%) |
|---|---|---|
| Vehicle | — | 100 |
| 1 | 0.1 | 75 |
| | 0.3 | 71 |
| | 1.0 | 61 |
| | 3.0 | 56 |
| 2 | 0.3 | 95 |
| | 1.0 | 89 |
| | 3.0 | 70 |

| Example No. | Rat Dose (mg/kg) of the title compound | Blood Glucose (%) |
|---|---|---|
| Vehicle | — | 100 |
| 27 | 3.0 | 79 |
| 41 | 1.0 | 60 |
| 66 | 0.1 | 92 |
| | 0.3 | 85 |
| | 1.0 | 58 |
| | 3.0 | 50 |
| 68 | 0.3 | 68 |
| | 1.0 | 58 |
| | 3.0 | 52 |

What is claimed is:

1. A compound represented by the formula

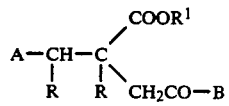

wherein A represents a thienyl group, a furyl group, a pyridyl group, a 3 to 8-membered cycloalkyl group or a phenyl group which may have one or more substituents selected from the group of a halogen atom, a lower alkyl group having 1 to 6 carbon atoms and a lower alkoxy group having 1 to 6 carbon atoms; B represents a bicyclic amino group which consists of a 5 or 6-membered cyclic amino ring fused with a 5 or 6-membered cycloalkyl ring, which may have 1 or 2 unsaturated bonds, with the proviso that B bonds to the carbon atom of the carbonyl group at the nitrogen atom; R represents a hydrogen atom or combine with each other to form a chemical bond; R$^1$ represents a hydrogen atom, a lower alkyl group having 1 to 6 carbon atoms or an aralkyl group having 7 to 10 carbon atoms; when there is an asymmetric carbon atom; enantiomers thereof and racemic mixtures thereof; when there are geometrical isomers, each geometrical isomer, E-isomers thereof, Z-isomers thereof, cis-isomers thereof and trans-isomers thereof; and pharmaceutically acceptable salts thereof.

2. A compound as claimed in claim 1, represented by the formula:

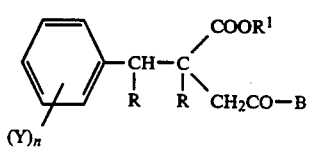

wherein B represents a bicyclic amino group which consists of a 5 or 6-membered cyclic amino ring fused with a 5 or 6-membered cycloalkyl ring, which may have 1 or 2 unsaturated bonds, with the proviso that B bonds to the carbon atom of the carbonyl group at the nitrogen atom; R represents a hydrogen atom or combine with each other to form a chemical bond; $R^1$ represents a hydrogen atom, a lower alkyl group having 1 to 6 carbon atoms or an aralkyl group having 7 to 10 carbon atoms; Y represents a halogen atom, a lower alkyl group having 1 to 6 carbon atoms or a lower alkoxy group having 1 to 6 carbon atoms; n represents 0, 1 or 2; when there is an asymmetric carbon atom, enantiomers thereof and racemic mixtures thereof; when there are geometrical isomers, each geometrical isomer, E-isomers thereof, Z-isomers thereof, cis-isomers thereof and trans-isomers thereof; and pharmaceutically acceptable salts thereof.

3. A compound as claimed in claim 2, represented by the formula:

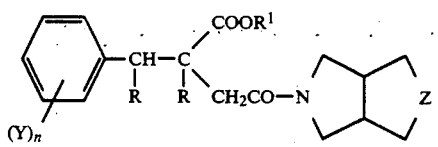

wherein R represents a hydrogen atom or combine with each other to form a chemical bond; $R^1$ represents a hydrogen atom, a lower alkyl group having 1 to 6 carbon atoms or an aralkyl group having 7 to 10 carbon atoms; Y represents a halogen atom, a lower alkyl group having 1 to 6 carbon atoms or a lower alkoxy group having 1 to 6 carbon atoms; n represents 0, 1 or 2; Z represents an ethylene group or a vinylene group; when there is an asymmetric carbon atom, enantiomers thereof and racemic mixtures thereof; when there are geometrical isomers, each geometrical isomer, E-isomers thereof, Z-isomers thereof, cis-isomers thereof and trans-isomers thereof; and pharmaceutically acceptable salts thereof.

4. A compound as claimed in claim 3, represented by the formula:

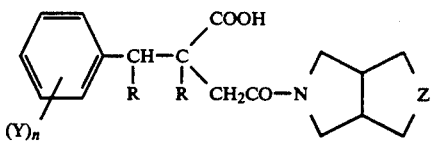

wherein R represents a hydrogen atom or combine with each other to form a chemical bond; Y represents a halogen atom, a lower alkyl group having 1 to 6 carbon atoms or a lower alkoxy group having 1 to 6 carbon atoms; n represents 0, 1 or 2; Z represents an ethylene group or a vinylene group; when there is an asymmetric carbon atom, enantiomers thereof and racemic mixtures thereof; when there are geometrical isomers, each geometrical isomer, E-isomers thereof, Z-isomers thereof, cis-isomers thereof and trans-isomers thereof; and pharmaceutically acceptable salts thereof.

5. The compound as claimed in claim 4, represented by the formula:

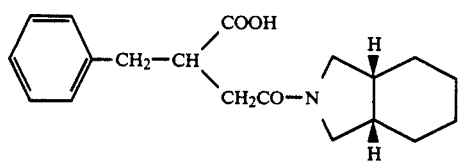

and enantiomers thereof and racemic mixtures thereof; and pharmaceutically acceptable salts thereof.

6. The compound as claimed in claim 5, represented by the formula:

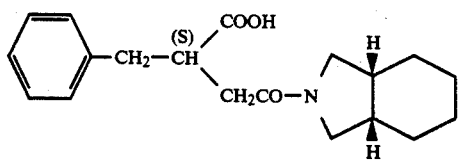

wherein C marked with (S) represents a carbon atom in S-configuration; and the pharmaceutically acceptable salts thereof.

7. A succinic acid compound selected from the group consisting of
(E)-2-benzylidene-3-(cis-hexahydro-2-isoindolinylcarbonyl)propionic acid,
(E)-2-benzylidene-3-(cis-3a,4,7,7a-tetrahydro-2-isoindolinylcarbonyl)propionic acid,
(E)-2-benzylidene-3-(trans-decahydro-2-isoquinolylcarbonyl)propionic acid,
(E)-2-benzylidene-3-(trans-hexahydro-1-indolinylcarbonyl)propionic acid,
(E)-2-benzylidene-3-(trans-hexahydro-2-isoindolinylcarbonyl)propionic acid,
(E)-2-(4-methylbenzylidene)-3-(cis-3a,4,7,7a-tetrahydro-2-isoindolinylcarbonyl)propionic acid,
(E)-2-(3-methylbenzylidene)-3-(cis-3a4,7,7a-tetrahydro-2-isoindolinylcarbonyl)propionic acid,
(E)-2-(4-methoxybenzylidene)-3-(cis-3a,4,7,7a-tetrahydro-2-isoindolinylcarbonyl)propionic acid,
(E)-3-(cis-hexahydro-2-isoindolinylcarbonyl)-2-(4-methylbenzylidene)propionic acid,
(E)-3-(cis-hexahydro-2-isoindolinylcarbonyl)-2-( 2-methylbenzylidene)propionic acid,
(E)-3-(cis-hexahydro-2-isoindolinylcarbonyl)-2-(2-isopropylbenzylidene)propionic acid,
(E)-2-(4-chlorobenzylidene)-3-(cis-hexahydro-2-isoindolinylcarbonyl)propionic acid,
(E)-2-(2-chlorobenzylidene)-3-(cis-hexahydro-2-isoindolinylcarbonyl)propionic acid,
(E)-2-(2-fluorobenzylidene)-3-(cis-hexahydro-2-isoindolinylcarbonyl)propionic acid,
(E)-3-(cis-hexahydro-2-isoindolinylcarbonyl)-2-(2-methoxybenzylidene)propionic acid,
(E)-2-(2-ethoxybenzylidene)-3-(cis-hexahydro-2-isoindolinylcarbonyl)propionic acid,
(E)-3-(cis-hexahydro-2-isoindolinylcarbonyl)-2-(2-propoxybenzylidene)propionic acid,
(Z)-2-(2,6-dimethylbenzylidene)-3-(cis-hexahydro-2-isoindolinylcarbonyl)propionic acid,
(E)-2-(2,6-dichlorobenzylidene)-3-(cis-hexahydro-2-isoindolinylcarbonyl)propionic acid,
(E)-2-(2,6-dimethoxybenzylidene)-3-(cis-hexahydro-2-isoindolinylcarbonyl)propionic acid,
(E)-3-(cis-hexahydro-2-isoindolinylcarbonyl)-2-(2-thenylidene)propionic acid, (E)-2-cyclohexylmethylene-3-(cis-hexahydro-2-isoindolinylcarbonyl)propionic acid,
(Z)-2-benzylidene-3-(cis-hexahydro-2-isoindolinylcarbonyl)propionic acid,
sodium (E)-2-benzylidene-3-(cis-hexahydro-2-isoindolinylcarbonyl)propionate,
sodium (E)-2-benzylidene-3-(cis-3a,4,7,7a-tetrahydro-2-isoindolinylcarbonyl)propionate,
methyl (E)-2-benzylidene-3-(cis-hexahydro-2-isoindolinylcarbonyl)propionate,
methyl (E)-2-benzylidene-3-(cis-3a,4,7,7a-tetrahydro-2-isoindolinylcarbonyl)propionate,
methyl (E)-2-(3-methylbenzylidene)-3-(cis-3a,4,7,7a-tetrahydro-2-isoindolinylcarbonyl)propionate,
methyl (E)-2-(4-methoxybenzylidene)-3-(cis-3a,4,7,7a-tetrahydro-2-isoindolinylcarbonyl)propionate,
methyl (E)-3-(cis-hexahydro-2-isoindolinylcarbonyl)-2-(2-methylbenzylidene)propionate,
methyl(E)-2-(4-chlorobenzylidene)-3-(cis-hexahydro-2-isoindolinylcarbonyl)propionate,
benzyl (E)-2-benzylidene-3-(cis-hexahydro-2-isoindolinylcarbonyl)propionate,
propyl (E)-2-benzylidene-3-(cis-hexahydro-2-isoindolinylcarbonyl)propionate,
propyl (E)-2-(4-methylbenzylidene)3-(cis-3a,4,7,7 a-tetrahydro-2-isoindolinylcarbonyl)propionate,
propyl (E)-2-(2-chlorobenzylidene)-3-(cis-hexahydro-2-isoindolinylcarbonyl)propionate,
2-benzyl-3-(trans-decahydro-2-isoquinolylcarbonyl)propionic acid,
2-benzyl-3-(trans-hexahydro-2-isoindolinylcarbonyl)propionic acid,
2-benzyl-3-(trans-hexahydro-1-indolinylcarbonyl)-propionic acid,
2-benzyl-3-(cis-hexahydro-2-isoindolinylcarbonyl)-propionic acid,
benzyl (S)-2-benzyl-3-(cis-hexahydro-2-isoindolinylcarbonyl)propionate,
(S)-2-benzyl-3-(cis-hexahydro-2-isoindolinylcarbonyl)propionic acid,
benzyl (R)-2-benzyl-3-(cis-hexahydro-2-isoindolinylcarbonyl)propionate,
(R)-2-benzyl-3-(cis-hexahydro-2-isoindolinylcarbonyl)propionic acid,
propyl 2-benzyl-3-(cis-3a,4,7,7a-tetrahydro-2-isoindolinylcarbonyl)propionate,
2-benzyl-3-(cis-3a,4,7,7a-tetrahydro-2-isoindolinylcarbonyl)propionic acid,
2-(4-methylbenzyl)-3-(cis-3a,4,7,7a-tetrahydro- 2-isoindolinylcarbonyl)propionic acid,
3-(cis-hexahydro-2-isoindolinylcarbonyl)-2-(4-methylbenzyl)propionic acid,
3-(cis-hexahydro-2-isoindolinylcarbonyl)-2-(2-methylbenzyl)propionic acid,
3-(cis-hexahydro- 2-isoindolinylcarbonyl)-2-(3-methylbenzyl)propionic acid,
3-(cis-hexahydro-2-isoindolinylcarbonyl)-2-(2-isopropylbenzyl)propionic acid,
3-(cis-hexahydro-2-isoindolinylcarbonyl)-2-(4methoxybenzyl)propionic acid,
3-(cis-hexahydro-2-isoindolinylcarbonyl)-2-(2-methoxybenzyl)propionic acid, 2(2-ethoxybenzyl)-3-(cis-hexahydro-2-isoindolinylcarbonyl)propionic acid,
3-(cis-hexahydro-2-isoindolinylcarbonyl)-2-(2-propoxybenzyl)propionic acid,
2-(2,6-dimethylbenzyl)-3-(cis-hexahydro-2-isoindolinylcarbonyl)propionic acid,
2-(2,6-dimethoxybenzyl)-3-(cis-hexahydro-2-isoindolinylcarbonyl)propionic acid,
3-(cis-hexahydro-2-isoindolinylcarbonyl)-2-(2-thenyl)-propionic acid,
2-cyclohexylmethyl-3-(cis-hexahydro- 2-isoindolinylcarbonyl)propionic acid,
methyl 2-benzyl-3-(cis-hexahydro-2-isoindolinylcarbonyl)propionate,
methyl 3-(cis-hexahydro-2-isoindolinylcarbonyl)-2-(4-methylbenzyl)propionate,
methyl 3-(cis-hexahydro-2-isoindolinylcarbonyl)-2-(2-methylbenzyl)propionate,
methyl 3-(cis-hexahydro-2-isoindolinylcarbonyl)-2-(3-methylbenzyl)propionate,
propyl 2-benzyl-3-(cis-hexahydro-2-isoindolinylcarbonyl)propionate,
propyl 3-(cis-hexahydro-2-isoindolinylcarbonyl)-2-(4-methylbenzyl)propionate,
propyl 3-(cis-hexahydro-2-isoindolinylcarbonyl)-2-(4-methoxybenzyl)propionate,
sodium (S)-2-benzyl-3-(cis-hexahydro-2-isoindolinylcarbonyl)propionate monohydrate,
potassium (S)-2-benzyl-3-(cis-hexahydro-2isoindolinylcarbonyl)propionate monohydrate,
calcium bis(S)-2-benzyl-3-(cis-hexahydro-2-isoindolinylcarbonyl)propionate dihydrate,
L-arginine salt of (S)-2-benzyl-3-(cis-hexahydro-2-isoindolinylcarbonyl)propionic acid and D-phenylalaninol salt of (S)-2-benzyl-3-(cis-hexahydro-2-isoindolinylcarbonyl)propionic acid.

8. A pharmaceutical composition containing, as an active ingredient, a succinic acid compound or a pharmaceutically acceptable salt thereof as claimed in claim 1 in combination with a pharmaceutically acceptable carrier.

9. A method for the treatment of diabetes which comprises administering a therapeutically effective amount of a succinic acid compound or a pharmaceutically acceptable salt thereof as claimed in claim 1.

* * * * *